United States Patent
Boden et al.

(10) Patent No.: US 7,045,614 B1
(45) Date of Patent: May 16, 2006

(54) LIM MINERALIZATION PROTEIN SPLICE VARIANTS

(75) Inventors: Scott D. Boden, Atlanta, GA (US); Gregory A. Hair, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/959,578

(22) PCT Filed: Apr. 28, 2000

(86) PCT No.: PCT/US00/11664

§ 371 (c)(1),
(2), (4) Date: Jun. 21, 2002

(87) PCT Pub. No.: WO00/66178

PCT Pub. Date: Nov. 9, 2000

Related U.S. Application Data

(60) Provisional application No. 60/132,021, filed on Apr. 30, 1999.

(51) Int. Cl.
*C07H 21/04* (2006.01)

(52) U.S. Cl. .................................... 536/23.5
(58) Field of Classification Search ............... None
See application file for complete search history.

(56) References Cited

FOREIGN PATENT DOCUMENTS

WO          WO 99/06563         2/1999

OTHER PUBLICATIONS

Boden, et al., 1998, Endocrinology, 139: 5125-5134.*
Kitty et al. 1999, Eur. J. Biochem., 266: 83-93.*
Olsen et al., 1999, Molecular Brain Research, 64: 255-263.*
Y. Liu et al., "BMP-6 Induces a Novel Lim Protein Involved in Bone Mineralization and Osteocalcin Secretion", Juornal of Bone and Mineral Research, NY, US, 12:49 (Aug. 1, 1997).*
D.M. Kingsley, "What Do BMPs Do in Mammals? Cluses From the Mouse Short-Ear Mutation", TIG, vol. 10, No. 1, Jan. 1994.
S.D. Boden et al., "LMP-1, A Lim-Domain Protein, Mediates BMP-6 Effects on Bone Formation", Endocrinology, vol. 139, No. 12, pp. 5125-5134, May 1998.
B.L.M. Hogan, "Bone Morphogenetic Proteins: Multifunctional Regulators of Vertebrate Development", Genes and Development, vol. 10, pp. 1580-1594, 1996.

* cited by examiner

*Primary Examiner*—Dave Trong Nguyen
*Assistant Examiner*—Joanne Hama
(74) *Attorney, Agent, or Firm*—Elmore Patent Law Group, pc; Darlene A. Vanstone; Carolyn S. Elmore

(57) ABSTRACT

The present invention is directed to isolated nucleic acid molecules that encode LIM mineralization protein, or LMP. The invention further provides vectors comprising splice variants of nucleotide sequences that encode LMP, as well as host cells comprising those vectors. Moreover, the present invention relates to methods of inducing bone formation by transfecting osteogenic precursor cells with an isolated nucleic acid molecule comprising a nucleotide sequence encoding splice variants of LIM mineralization protein. The transfection may occur ex vivo or in vivo by direct injection of virus or naked plasmid DNA. In a particular embodiment, the invention provides a method of fusing a spine by transfecting osteogenic precursor cells with an isolated nucleic acid molecule having a nucleotide sequence encoding LIM mineralization protein, admixing the transfected osteogenic precursor cells with a matrix and contacting the matrix with the spine. Finally, the invention relates to methods for inducing systemic bone formation by stable transfection of host cells with the vectors of the invention.

3 Claims, No Drawings

LIM MINERALIZATION PROTEIN SPLICE VARIANTS

CROSS REFERENCE TO RELATED APPLICATIONS

This application is a national phase entry of international application number PCT/US00/11664, filed Apr. 28, 2000, and claims the benefit of U.S. Provisional Application No. 60/132,021, filed Apr. 30, 1999, the content of which is incorporated herein by reference.

BACKGROUND OF THE INVENTION

1. Field of the Invention

The field of the invention relates generally to osteogenic cells and the formation of bone and boney tissue in mammalian species. Specifically, the invention concerns a novel family of proteins, and nucleic acids encoding those proteins, that enhances the efficacy of bone mineralization in vitro and in vivo. The invention provides methods for treating a variety of pathological conditions associated with bone and boney tissue, such as, for example, spine fusion, fracture repair and osteoporosis.

2. Description of the Related Art

Osteoblasts are thought to differentiate from pluripotent mesenchymal stem cells. The maturation of an osteoblast results in the secretion of an extracellular matrix which can mineralize and form bone. The regulation of this complex process is not well understood but is thought to involve a group of signaling glycoproteins known as bone morphogenetic proteins (BMPs). These proteins have been shown to be involved with embryonic dorsal-ventral patterning, limb bud development, and fracture repair in adult animals. B. L. Hogan, *Genes & Develop*, 10:1580 (1996). This group of transforming growth factor-beta superfamily secreted proteins has a spectrum of activities in a variety of cell types at different stages of differentiation; differences in physiological activity between these closely related molecules have not been clarified. D. M. Kingsley, *Trends Genet.*, 10:16 (1994).

To better discern the unique physiological role of different BMP signaling proteins, we recently compared the potency of BMP-6 with that of BMP-2 and BMP-4, for inducing rat calvarial osteoblast differentiation. Boden et al., *Endocrinology*, 137:3401 (1996). We studied this process in first passage (secondary) cultures of fetal rat calvaria that require BMP or glucocorticoid for initiation of differentiation. In this model of membranous bone formation, glucocorticoid (GC) or a BMP will initiate differentiation to mineralized bone nodules capable of secreting osteocalcin, the osteoblast-specific protein. This secondary culture system is distinct from primary rat osteoblast cultures which undergo spontaneous differentiation. In this secondary system, glucocorticoid resulted in a ten-fold induction of BMP-6 mRNA and protein expression which was responsible for the enhancement of osteoblast differentiation. Boden et al., *Endocrinology*, 138:2920 (1997).

In addition to extracellular signals, such as the BMPs, intracellular signals or regulatory molecules may also play a role in the cascade of events leading to formation of new bone. One broad class of intracellular regulatory molecules are the LIM proteins, which are so named because they possess a characteristic structural motif known as the LIM domain. The LIM domain is a cysteine-rich structural motif composed of two special zinc fingers that are joined by a 2-amino acid spacer. Some proteins have only LIM domains, while others contain a variety of additional functional domains. LIM proteins form a diverse group, which includes transcription factors and cytoskeletal proteins. The primary role of LIM domains appears to be in mediating protein—protein interactions, through the formation of dimers with identical or different LIM domains, or by binding distinct proteins.

In LIM homeodomain proteins, that is, proteins having both LIM domains and a homeodomain sequence, the LIM domains function as negative regulatory elements, LIM homeodomain proteins are involved in the control of cell lineage determination and the regulation of differentiation, although LIM-only proteins may have similar roles. LIM-only proteins are also implicated in the control of cell proliferation since several genes encoding such proteins are associated with oncogenic chromosome translocations.

Humans and other mammalian species are prone to diseases or injuries that require the processes of bone repair and/or regeneration. For example, treatment of fractures would be improved by new treatment regimens that could stimulate the natural bone repair mechanisms, thereby reducing the time required for the fractured bone to heal. In another example, individuals afflicted with systemic bone disorders, such as osteoporosis, would benefit from treatment regimens that would results in systemic formation of new bone. Such treatment regimens would reduce the incidence of fractures arising from the loss of bone mass that is a characteristic of this disease.

For at least these reasons, extracellular factors, such as the BMPs, have been investigated for the purpose of using them to stimulate formation of new bone in vivo. Despite the early successes achieved with BMPs and other extracellular signalling molecules, their use entails a number of disadvantages. For example, relatively large doses of purified BMPs are required to enhance the production of new bone, thereby increasing the expense of such treatment methods. Furthermore, extracellular proteins are susceptible to degradation following their introduction into a host animal. In addition, because they are typically immunogenic, the possibility of stimulating an immune response to the administered proteins is ever present.

Due to such concerns, it would be desirable to have available treatment regimens that use an intracellular signalling molecule to induce new bone formation. Advances in the field of gene therapy now make it possible to introduce into osteogenic precursor cells, that is, cells involved in bone formation, or peripheral blood leukocytes, nucleotide fragments encoding intracellular signals that form part of the bone formation process. Gene therapy for bone formation offers a number of potential advantages: (1) lower production costs; (2) greater efficacy, compared to extracellular treatment regiments, due to the ability to achieve prolonged expression of the intracellular signal; (3) it would by-pass the possibility that treatment with extracellular signals might be hampered due to the presence of limiting numbers of receptors for those signals; (4) it permits the delivery of transfected potential osteoprogenitor cells directly to the site where localized bone formation is required; and (5) it would permit systemic bone formation, thereby providing a treatment regimen for osteoporosis and other metabolic bone diseases.

SUMMARY OF THE INVENTION

The present invention seeks to overcome the drawbacks in the prior art by providing novels compositions and methods for inducing bone formation using an intracellular signalling molecule that participates early in the cascade of events that leads to bone formation. Applicants have discovered 10-4/ RLMP (SEQ ID NO: 1, SEQ ID NO: 2), a novel LIM gene with a sequence originally isolated from stimulated rat calvarial osteoblast cultures. The gene has been cloned, sequenced and assayed for its ability to enhance the efficacy of bone mineralization in vitro. The protein RLMP affects mineralization of bone matrix as well as differentiation of cells into the osteoblast lineage. Unlike other known cytokines, for example, BMPs, RLMP is not a secreted protein, but is instead an intracellular signaling molecule. This feature has the advantage of providing intracellular signaling amplification as well as easier assessment of transfected cells. It is also suitable for more efficient and specific in vivo applications. Suitable clinical applications include enhancement of bone repair in fractures, bone defects, bone grafting, and normal homeostasis in patients presenting with osteoporosis.

Applicants have also cloned, sequenced and deduced the amino acid sequence of a corresponding human protein, named human LMP-1. The human protein demonstrates enhanced efficacy of bone mineralization in vitro and in vivo.

In addition, the applicants have characterized a truncated (short) version of LMP-1, termed HLMP-1s. This short version resulted from a point mutation in one source of a cDNA clone, providing a stop codon which truncated the protein. The short version (LMP-1s) is fully functional when expressed in cell culture and in vivo.

Using PCR analysis of human heart cDNA library, Applicants have identified two alternative splice variants (referred to as HLMP-2 and HLMP-3) that differ from HLMP-1 in a region between base pairs 325 and 444 in the nucleotide sequence encoding HLMP-1. The HLMP-2 sequence has a 119 base pair deletion and an insertion of 17 base pairs in this region. Compared to HLMP-1, the nucleotide sequence encoding HLMP-3 has no deletions, but it does have the same 17 base pairs as HLMP-2, which are inserted at position 444 in the HLMP-1 sequence.

Additional features and advantages of the invention will be set forth in the description which follows, and in part will be apparent from the description, or may be learned by practice of the invention. The objectives and other advantages of the invention will be realized and attained by the methods and compositions of matter particularly pointed out in the written description and claims hereof.

In one broad aspect, the invention relates to an isolated nucleic acid molecule comprising a nucleic acid sequence encoding any LIM mineralization protein, wherein the nucleic acid molecule hybridizes under standard conditions to a nucleic acid molecule complementary to the full length of SEQ. ID NO: 25, and wherein the molecule hybridizes under highly stringent conditions to a nucleic acid molecule complementary to the full length of SEQ. ID NO: 26. In a specific aspect, the isolated nucleic acid molecule encodes HLMP-1, HLMP-1s, RLMP, HLMP-2, or HLMP-3. In addition, the invention is directed to vectors comprising these nucleic acid molecules, as well as host cells comprising the vectors. In another specific aspect, the invention relates to the proteins themselves.

In a second broad aspect, the invention relates to antibody that is specific for LIM mineralization protein, including HLMP-1, HLMP-1s, RLMP, HLMP-2, and HLMP-3. In one specific aspect, the antibody is a polyclonal antibody. In another specific aspect, the antibody is a monoclonal antibody.

In a third broad aspect, the invention relates to method of inducing bone formation wherein osteogenic precursor cells are transfected with an isolated nucleic acid molecule comprising a nucleotide sequence encoding LIM mineralization protein. In one specific aspect, the isolated nucleic acid molecule is in a vector, which may be a plasmid or a virus, such as adenovirus or retrovirus. The transfection may occur ex vivo or in vivo by direct injection of the isolated nucleic acid molecule. The transfected isolated nucleic acid molecule may encode HLMP-1, HLMP-1s, RLMP, HLMP-2, or HLMP-3.

In a further aspect, the invention relates to methods of fusing a spine by transfecting osteogenic precursor cells with an isolated nucleic acid molecule having a nucleotide sequence encoding LIM mineralization protein, admixing the transfected osteogenic precursor cells with a matrix and contacting the matrix with the spine.

In yet another aspect, the invention relates to methods for inducing systemic bone formation by stable transfection of host cells with the vectors of the invention.

It is to be understood that both the foregoing general description and the following detailed description are exemplary and explanatory and are intended to provide further explanation of the invention as claimed.

| ABBREVIATIONS AND DEFINITIONS | |
|---|---|
| BMP | Bone Morphogenetic Protein |
| HLMP-1 | Human LMP-1, also designated as Human LIM Protein or HLMP |
| HLMP-1s | Human LMP-1 Short (truncated) protein |
| HLMPU | Human LIM Protein Unique Region |
| LMP | LIM mineralization protein |
| MEM | Minimal essential medium |
| Trm | Triamcinolone |
| -GlyP | Beta-glycerolphosphate |
| RACE | Rapid Amplification of cDNA Ends |
| RLMP | Rat LIM mineralization protein, also designated as RLMP-1 |
| RLMPU | Rat LIM Protein Unique Region |
| RNAsin | RNase inhibitor |
| ROB | Rat Osteoblast |
| 10-4 | Clone containing cDNA sequence for RLMP (SEQ ID NO: 2) |
| UTR | Untranslated Region |
| HLMP-2 | Human LMP Splice Variant 2 |
| HLMP-3 | Human LMP Splice Variant 3 |

DETAILED DESCRIPTION OF THE INVENTION

The present invention relates to novel mammalian LIM proteins, herein designated LIM mineralization proteins, or LMP. The invention relates more particularly to human LMP, known as HLMP or HLMP-1, or alternative splice variants of human LMP, which are known as HLMP-2 or HLMP-3. The applicants have discovered that these proteins enhance bone mineralization in mammalian cells grown in vitro. When produced in mammals, LMP also induces bone formation in vivo.

Ex vivo transfection of bone marrow cells, osteogenic precursor cells, peripheral blood leukocytes, or mesenchymal stem cells with nucleic acid that encodes LMP or HLMP, followed by reimplantation of the transfected cells in the donor, is suitable for treating a variety of bone-related disorders or injuries. For example, one can use this method to: augment long bone fracture repair; generate bone in segmental defects; provide a bone graft substitute for fractures; facilitate tumor reconstruction or spine fusion; and provide a local treatment (by injection) for weak or osteoporotic bone, such as in osteoporosis of the hip, vertebrae, or wrist. Transfection with LMP or HLMP-encoding nucleic acid is also useful in: the percutaneous injection of transfected marrow cells to accelerate the repair of fractured long bones; treatment of delayed union or non-unions of long bone fractures or pseudoarthrosis of spine fusions; and for inducing new bone formation in avascular necrosis of the hip or knee.

In addition to ex vivo-based methods of gene therapy, transfection of a recombinant DNA vector comprising a nucleic acid sequence that encodes LMP or HLMP can be accomplished in vivo. When a DNA fragment that encodes LMP or HLMP is inserted into an appropriate viral vector, for example, an adenovirus vector, the viral construct can be injected directly into a body site were endochondral bone formation is desired. By using a direct, percutaneous injection to introduce the LMP or HLMP sequence stimulation of bone formation can be accomplished without the need for surgical intervention either to obtain bone marrow cells (to transfect ex vivo) or to reimplant them into the patient at the site where new bone is required. Alden et al., *Neurosurgical Focus* (1998), have demonstrated the utility of a direct injection method of gene therapy using a cDNA that encodes BMP-2, which was cloned into an adenovirus vector.

It is also possible to carry out in vivo gene therapy by directly injecting into an appropriate body site, a naked, that is, unencapsulated, recombinant plasmid comprising a nucleic acid sequence that encodes HLMP. In this embodiment of the invention, transfection occurs when the naked plasmid DNA is taken up, or internalized, by the appropriate target cells, which have been described. As in the case of in vivo gene therapy using a viral construct, direct injection of naked plasmid DNA offers the advantage that little or no surgical intervention is required. Direct gene therapy, using naked plasmid DNA that encodes the endothelial cell mitogen VEGF (vascular endothelial growth factor), has been successfully demonstrated in human patients. Baumgartner et al., *Circulation*, 97 (12):1114–23 (1998).

By using an adenovirus vector to deliver LMP into osteogenic cells, transient expression of LMP is achieved. This occurs because adenovirus does not incorporate into the genome of target cells that are transfected. Transient expression of LMP, that is, expression that occurs during the lifetime of the transfected target cells, is sufficient to achieve the objects of the invention. Stable expression of LMP, however, can occur when a vector that incorporates into the genome of the target cell is used as a delivery vehicle. Retrovirus-based vectors, for example, are suitable for this purpose.

Stable expression of LMP is particularly useful for treating various systemic bone-related disorders, such as osteoporosis and osteogenesis imperfecta. For this embodiment of the invention, in addition to using a vector that integrates into the genome of the target cell to deliver an LMP-encoding nucleotide sequence into target cells, LMP expression is placed under the control of a regulatable promoter. For example, a promoter that is turned on by exposure to an exogenous inducing agent, such as tetracycline, is suitable. Using this approach, one can stimulate formation of new bone on a systemic basis by administering an effective amount of the exogenous inducing agent. Once a sufficient quantity of bone mass is achieved, administration of the exogenous inducing agent is discontinued. This process may be repeated as needed to replace bone mass lost, for example, as a consequence of osteoporosis.

Antibodies specific for HLMP are particularly suitable for use in methods for assaying the osteoinductive, that is, bone-forming, potential of patient cells. In this way one can identify patients at risk for slow or poor healing of bone repair. Also, HLMP-specific antibodies are suitable for use in marker assays to identify risk factors in bone degenerative diseases, such as, for example, osteoporosis.

Following well known and conventional methods, the genes of the present invention are prepared by ligation of nucleic acid segments that encode LMP to other nucleic acid sequences, such as cloning and/or expression vectors. Methods needed to construct and analyze these recombinant vectors, for example, restriction endonuclease digests, cloning protocols, mutagenesis, organic synthesis of oligonucleotides and DNA sequencing, have been described. For DNA sequencing DNA, the dieoxyterminator method is the preferred.

Many treatises on recombinant DNA methods have been published, including Sambrook et al., *Molecular Cloning: A Laboratory Manual*, Cold Spring Harbor Press, 2nd edition (1988), Davis et al., *Basic Methods in Molecular Biology*, Elsevier (1986), and Ausubel et al., *Current Protocols in Molecular Biology*, Wiley Interscience (1988). These reference manuals are specifically incorporated by reference herein.

Primer-directed amplification of DNA or cDNA is a common step in the expression of the genes of this invention. It is typically performed by the polymerase chain reaction (PCR). PCR is described in U.S. Pat. No. 4,800,159 to Mullis et al., and other published sources. The basic principle of PCR is the exponential replication of a DNA sequence by successive cycles of primer extension. The extension products of one primer, when hybridized to another primer, becomes a template for the synthesis of another nucleic acid molecule. The primer-template complexes act as substrate for DNA polymerase, which in performing its replication function, extends the primers. The conventional enzyme for PCR applications is the thermostable DNA polymerase isolated from *Thermus aquaticus*, or Taq DNA polymerase.

Numerous variations of the basic PCR method exist, and a particular procedure of choice in any given step needed to construct the recombinant vectors of this invention is readily performed by a skilled artisan. For example, to measure cellular expression of 10-4/RLMP, RNA is extracted and reverse transcribed under standard and well known procedures. The resulting cDNA is then analyzed for the appropriate mRNA sequence by PCR.

The gene encoding the LIM mineralization protein is expressed in an expression vector in a recombinant expression system. Of course, the constructed sequence need not be the same as the original, or its complimentary sequence, but instead may be any sequence determined by the degeneracy of the DNA code that nonetheless expresses an LMP having bone forming activity. Conservative amino acid substitutions, or other modifications, such as the occurrence of an amino-terminal methionine residue, may also be employed.

A ribosome binding site active in the host expression system of choice is ligated to the 5' end of the chimeric LMP coding sequence, forming a synthetic gene. The synthetic gene can be inserted into any one of a large variety of vectors for expression by ligating to an appropriately linearized plasmid. A regulatable promoter, for example, the *E. coli* lac promoter, is also suitable for the expression of the chimeric coding sequences. Other suitable regulatable promoters include trp, tac, recA, T7 and lambda promoters.

DNA encoding LMP is transfected into recipient cells by one of several standard published procedures, for example, calcium phosphate precipitation, DEAE-Dextran, electroporation or protoplast fusion, to form stable transformants. Calcium phosphate precipitation is preferred, particularly when performed as follows.

DNAs are coprecipitated with calcium phosphate according to the method of Graham and Van Der, *Virology*, 52:456 (1973), before transfer into cells. An aliquot of 40–50 g of DNA, with salmon sperm or calf thymus DNA as a carrier, is used for $0.5 \times 10^6$ cells plated on a 100 mm dish. The DNA is mixed with 0.5 ml of 2× Hepes solution (280 mM NaCl, 50 mM Hepes and 1.5 mM $Na_2HPO_4$, pH 7.0), to which an equal volume of 2× $CaCl_2$ (250 mM $CaCl_2$ and 10 mM Hepes, pH 7.0) is added. A white granular precipitate, appearing after 30–40 minutes, is evenly distributed dropwise on the cells, which are allowed to incubate for 4–16 hours at 37° C. The medium is removed and the cells shocked with 15% glycerol in PBS for 3 minutes. After removing the glycerol, the cells are fed with Dulbecco's Minimal Essential Medium (DMEM) containing 10% fetal bovine serum.

DNA can also be transfected using: the DEAE-Dextran methods of Kimura et al., *Virology*, 49:394 (1972) and Sompayrac et al., *Proc. Natl. Acad. Sci. USA*, 78:7575 (1981); the electroporation method of Potter, *Proc. Natl. Acad. Sci. USA*, 81:7161 (1984); and the protoplast fusion method of Sandri-Goddin et al., *Molec. Cell. Biol.*, 1:743 (1981).

Phosphoramidite chemistry in solid phase is the preferred method for the organic synthesis of oligodeoxynucleotides and polydeoxynucleotides. In addition, many other organic synthesis methods are available. Those methods are readily adapted by those skilled in the art to the particular sequences of the invention.

The present invention also includes nucleic acid molecules that hybridize under standard conditions to any of the nucleic acid sequences encoding the LIM mineralization proteins of the invention. "Standard hybridization conditions" will vary with the size of the probe, the background and the concentration of the nucleic acid reagents, as well as the type of hybridization, for example, in situ, Southern blot, or hybrization of DNA-RNA hybrids (Northern blot). The determination of "standard hybridization conditions" is within the level of skill in the art. For example, see U.S. Pat. No. 5,580,775 to Fremeau et al., herein incorporated by reference for this purpose. See also, Southern, E. M., *J. Mol. Biol.*, 98:503 (1975), Alwine et al., *Meth. Enzymol.*, 68:220 (1979), and Sambrook et al., *Molecular Cloning: A laboratory Manual*, 2nd edition, pp. 7.19–7.50, Cold Spring Harbor Press (1989).

One preferred set of standard hybrization conditions involves a blot that is prehybridized at 42° C. for 2 hours in 50% formamide, 5× SSPE (150 nM NaCl, 10 mM Na $H_2PO_4$ [pH 7.4], 1 mM EDTA [pH 8.0]), 5× Denhardt's solution (20 mg Ficoll, 20 mg polyvinylpyrrolidone and 20 mg BSA per 100 ml water), 10% dextran sulphate, 1% SDS and 100 g/ml salmon sperm DNA. A $^{32}$P-labelled cDNA probe is added, and hybridization is continued for 14 hours. Afterward, the blot is washed twice with 2× SSPE, 0.1% SDS for 20 minutes at 22° C., followed by a 1 hour wash at 65° C. in 0.1× SSPE, 0.1% SDS. The blot is then dried and exposed to x-ray film for 5 days in the presence of an intensifying screen.

Under "highly stringent conditions," a probe will hybridize to its target sequence if those two sequences are substantially identical. As in the case of standard hybridization conditions, one of skill in the art can, given the level of skill in the art and the nature of the particular experiment, determine the conditions under which only susbstantially identical sequences will hybridize.

Another aspect of the invention includes the proteins encoded by the nucleic acid sequences. In still another embodiment, the inventon relates to the identification of such proteins based on anti-LMP antibodies. In this embodiment, protein samples are prepared for Western blot analysis by lysing cells and separating the proteins by SDS-PAGE. The proteins are transferred to nitrocellulose by electroblotting as described by Ausubel et al., *Current Protocols in Molecular Biology*, John Wiley and Sons (1987). After blocking the filter with instant nonfat dry milk (1 gm in 100 ml PBS), anti-LMP antibody is added to the filter and incubated for 1 hour at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Monospecific antibodies are the reagent of choice in the present invention, and are specifically used to analyze patient cells for specific characteristics associated with the expression of LMP. "Monospecific antibody" as used herein is defined as a single antibody species or multiple antibody species with homogenous binding characteristics for LMP. "Homogeneous binding" as used herein refers to the ability of the antibody species to bind to a specific antigen or epitope, such as those associated with LMP, as described above. Monospecific antibodies to LMP are purified from mammalian antisera containing antibodies reactive against LMP or are prepared as monoclonal antibodies reactive with LMP using the technique of Kohler and Milstein, *Nature*, 256:495–97 (1975). The LMP specific antibodies are raised by immunizing animals such as, for example, mice, rats, guinea pigs, rabbits, goats or horses, with an appropriate concentration of LMP either with or without an immune adjuvant.

In this process, preimmune serum is collected prior to the first immunization. Each animal receives between about 0.1 mg and about 1000 mg of LMP associated with an acceptable immune adjuvant, if desired. Such acceptable adjuvants include, but are not limited to, Freund's complete, Freund's incomplete, alum-precipitate, water in oil emulsion containing *Corynebacterium parvum* and tRNA adjuvants. The initial immunization consists of LMP in, preferably, Freund's complete adjuvant injected at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with LMP are prepared by immunizing inbred mice, preferably Balb/c mice, with LMP. The mice are immunized by the IP or SC route with about 0.1 mg to about 10 mg, preferably about 1 mg, of LMP in about 0.5 ml buffer or saline incorporated in an equal volume of an acceptable adjuvant, as discussed above. Freund's complete adjuvant is preferred. The mice receive an initial immunization on day 0 and are rested for about 3–30 weeks. Immunized mice are given one or more booster immunizations of about 0.1 to about 10 mg of LMP in a buffer solution such as phosphate buffered saline by the intravenous (IV) route Lymphocytes from antibody-positive mice, preferably splenic lymphocytes, are obtained by removing the spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin in supplemented Dulbecco's Modified Eagles Medium (DMEM) by procedures known in the art. Supernatant fluids are collected from growth positive wells on about days 14, 18, and 21, and are screened for antibody production by an immunoassay such as solid phase immunoradioassay (SPIRA) using LMP as the antigen. The culture fluids are also tested in the Ouchterlony precipitation assay to determine the isotype of the mAb. Hybridoma cells from antibody positive wells are cloned by a technique such as the soft agar technique of MacPherson, "Soft Agar Techniques", in *Tissue Culture Methods and Applications*, Kruse and Paterson (eds.), Academic Press (1973). See, also, Harlow et al., *Antibodies: A Laboratory Manual*, Cold Spring Laboratory (1988).

Monoclonal antibodies may also be produced in vivo by injection of pristane-primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production in anti-LMP mAb is carried out by growing the hydridoma cell line in DMEM containing about 2% fetal calf serum to obtain sufficient quantities of the specific mAb. The mAb are purified by techniques known in the art.

Antibody titers of ascites or hybridoma culture fluids are determined by various serological or immunological assays, which include, but are not limited to, precipitation, passive agglutination, enzyme-linked immunosorbent antibody (ELISA) technique and radioimmunoassay (RIA) techniques. Similar assays are used to detect the presence of the LMP in body fluids or tissue and cell extracts.

It is readily apparent to those skilled in the art that the above described methods for producing monospecific antibodies may be utilized to produce antibodies specific for polypeptide fragments of LMP, full-length nascent LMP polypeptide, or variants or alleles thereof.

In another embodiment, the invention is directed to alternative splice variants of HLMP-1. PCR analysis of human heart cDNA revealed mRNA for two HLMP alternative splice variants, named HLMP-2 and HLMP-3, that differ from HLMP-1 in a region between base pairs 325 and 444 in the hLMP-1 sequence. The HLMP-2 sequence has a 119 base pair deletion and an insertion of 17 base pairs in this region. These changes preserve the reading frame, resulting in a 423 amino acid protein, which compared to HLMP-1, has a net loss of 34 amino acids (40 amino acids deleted plus 6 inserted amino acids). HLMP-2 contains the c-terminal LIM domains that are present in HLMP-1.

Compared to HLMP-1, HLMP-3 has no deletions, but it does have the same 17 base pair insertion at position 444. This insertion shifts the reading frame, causing a stop codon at base pairs 459–461. As a result, HLMP-3 encodes a protein of 153 amino acids. This protein lacks the c-terminal LIM domains that are present in HLMP-1 and HLMP-2. The predicted size of the proteins encoded by HLMP-2 and HLMP-3 was confirmed by western blot analysis.

PCR analysis of the tissue distribution of the three splice variants revealed that they are differentially expressed, with specific isoforms predominating in different tissues. HLMP-1 is apparently the predominant form expressed in leukocytes, spleen, lung, placenta, and fetal liver. HLMP-2 appears to be the predominant isoform in skeletal muscle, bone marrow, and heart tissue. HLMP-3, however, was not the predominant isoform in any tissue examined.

Overexpression of HLMP-3 in secondary rat osteoblast cultures induced bone nodule formation (287±56) similar to the effect seen for glucicorticoid (272±7) and HLMP-1 (232±200). Since HLMP-3 lacks the C-terminal LIM domains, there regions are not required for osteoinductive activity. Overexpression of HLMP-2, however, did not induce nodule formation (11±3). These data suggest that the amino acids encoded by the deleted 119 base pairs are necessary for osteoinduction. The data also suggest that the distribution of HLMP splice variants may be important for tissue-specific function. Surprisingly, we have shown that HLMP-2 inhibits steroid-induced osteoblast formation in secondary rat osteoblast cultures. Therefore, HLMP-2 will have therapeutic utility in clinical situations where bone formation is not desirable.

On Jul. 22, 1997, a sample of 10-4/RLMP in a vector designated pCMV2/RLMP (which is vector pRc/CMV2 with insert 10-4 clone/RLMP) was deposited with the American Type Culture Collection (ATCC), 12301 Parklawn Drive, Rockville, Md. 20852. The culture accession number for that deposit is 209153. On Mar. 19, 1998, a sample of the vector pHis-A with insert HLPM-1s was deposited at the American Type Culture Collection ("ATCC"). The culture accession number for that deposit is 209698. On Apr. 14, 2000, samples of plasmids pHAhLMP-2 (vector pHisA with cDNA insert derived from human heart muscle cDNA with HLMP-2) and pHAhLMP-3 (vector pHisA with cDNA insert derived from human heart muscle cDNA with HLMP-3) were deposited with the ATCC, 10801 University Blvd., Manassas, Va., 20110-2209, USA, under the conditions of the Budapest treaty. The accession numbers for these deposits are PTA-1698 and PTA-1699, respectively. These deposits, as required by the Budapest Treaty, will be maintained in the ATCC for at least 30 years and will be made available to the public upon the grant of a patent disclosing them. It should be understood that the availability of a deposit does not constitute a license to practice the subject invention in derogation of patent rights granted by government action.

In assessing the nucleic acids, proteins, or antibodies of the invention, enzyme assays, protein purification, and other conventional biochemical methods are employed. DNA and RNA are analyzed by Southern blotting and Northern blotting techniques, respectively. Typically, the samples analyzed are size fractionated by gel electrophoresis. The DNA or RNA in the gels are then transferred to nitrocellulose or nylon membranes. The blots, which are replicas of sample patterns in the gels, were then hybridized with probes. Typically, the probes are radiolabelled, preferably with $^{32}P$, although one could label the probes with other signal-generating molecules known to those in the art. Specific bands of interest can then be visualized by detection systems, such as autoradiography.

For purposes of illustrating preferred embodiments of the present invention, the following, non-limiting examples are included. These results demonstrate the feasibility of inducing or enhancing the formation of bone using the LIM mineralization proteins of the invention, and the isolated nucleic acid molecules encoding those proteins.

EXAMPLE 1

Calvarial Cell Culture

Rat calvarial cells, also known as rat osteoblasts ("ROB"), were obtained from 20-day pre-parturition rats as previously described. Boden et al., Endocrinology, 137 (8):3401–07 (1996). Primary cultures were grown to confluence (7 days), trypsinized, and passed into 6-well plates ($1 \times 10^5$ cells/35 mm well) as first subculture cells. The subculture cells, which were confluent at day 0, were grown for an additional 7 days. Beginning on day 0, media were changed and treatments (Trm and/or BMPs) were applied, under a laminar flow hood, every 3 or 4 days. The standard culture protocol was as follows: days 1–7, MEM, 10% FBS, 50 g/ml ascorbic acid, ± stimulus; days 8–14, BGJb medium, 10% FBS, 5 mM-GlyP (as a source of inorganic phosphate to permit mineralization). Endpoint analysis of bone nodule formation and osteocalcin secretion was performed at day 14. The dose of BMP was chosen as 50 ng/ml based on pilot experiments in this system that demonstrated a mid-range effect on the dose-response curve for all BMPs studied.

EXAMPLE 2

Antisense Treatment and Cell Culture

To explore the potential functional role of LMP-1 during membranous bone formation, we synthesized an antisense oligonucleotide to block LMP-1 mRNA translation and treated secondary osteoblast cultures that were undergoing differentiation initiated by glucocorticoid. Inhibition of RLMP expression was accomplished with a highly specific antisense oligonucleotide (having no significant homologies to known rat sequences) corresponding to a 25 bp sequence spanning the putative translational start site (SEQ ID NO: 42). Control cultures either did not receive oligonucleotide or they received sense oligonucleotide. Experiments were performed in the presence (preincubation) and absence of lipofectamine. Briefly, 22 g of sense or antisense RLMP oligonucleotide was incubated in MEM for 45 minutes at room temperature. Following that incubation, either more MEM or pre-incubated lipofectamine/MEM (7% v/v; incubated 45 minutes at room temperature) was added to achieve an oligonucleotide concentration of 0.2 M. The resulting mixture was incubated for 15 minutes at room temperature. Oligonucleotide mixtures were then mixed with the appropriate medium, that is, MEM/Ascorbate/±Trm, to achieve a final oligonucleotide concentration of 0.1 M.

Cells were incubated with the appropriate medium (±stimulus) in the presence or absence of the appropriate oligonucleotides. Cultures originally incubated with lipofectamine were re-fed after 4 hours of incubation (37° C.; 5% $CO_2$) with media containing neither lipofectamine nor oligonucleotide. All cultures, especially cultures receiving oligonucleotide, were re-fed every 24 hours to maintain oligonucleotide levels.

LMP-1 antisense oligonucleotide inhibited mineralized nodule formation and osteocalcin secretion in a dose-dependent manner, similar to the effect of BMP-6 oligonucleotide. The LMP-1 antisense block in osteoblast differentiation could not be rescued by addition of exogenous BMP-6, while the BMP-6 antisense oligonucleotide inhibition was reversed with addition of BMP-6. This experiment further confirmed the upstream position of LMP-1 relative to BMP-6 in the osteoblast differentiation pathway. LMP-1 antisense oligonucleotide also inhibited spontaneous osteoblast differentiation in primary rat osteoblast cultures.

EXAMPLE 3

Quantitation of Mineralized Bone Nodule Formation

Cultures of ROBs prepared according to Examples 1 and 2 were fixed overnight in 70% ethanol and stained with von Kossa silver stain. A semi-automated computerized video image analysis system was used to quantitate nodule count and nodule area in each well. Boden et al., Endocrinology, 137 (8):3401–07 (1996). These values were then divided to calculate the area per nodule values. This automated process was validated against a manual counting technique and demonstrated a correlation coefficient of 0.92 ($p<0.000001$). All data are expressed as the mean±standard error of the mean (S.E.M.) calculated from 5 or 6 wells at each condition. Each experiment was confirmed at least twice using cells from different calvarial preparations.

EXAMPLE 4

Quantitation of Osteocalcin Secretion

Osteocalcin levels in the culture media were measured using a competitive radioimmunoassay with a monospecific polyclonal antibody (Pab) raised in our laboratory against the C-terminal nonapeptide of rat osteocalcin as described in Nanes et al., Endocrinology, 127:588 (1990). Briefly, 1 g of nonapeptide was iodinated with 1 mCi $^{125}$I-Na by the lactoperoxidase method. Tubes containing 200 1 of assay buffer (0.02 M sodium phosphate, 1 mM EDTA, 0.001% thimerosal, 0.025% BSA) received media taken from cell cultures or osteocalcin standards (0–12,000 fmole) at 100 l/tube in assay buffer. The Pab (1:40,000; 100 1) was then added, followed by the iodinated peptide (12,000 cpm; 100 l). Samples tested for non-specific binding were prepared similarly but contained no antibody.

Bound and free PAbs were separated by the addition of 700 1 goat anti-rabbit IgG, followed by incubation for 18 hours at 4° C. After samples were centrifuged at 1200 rpm for 45 minutes, the supernatants were decanted and the precipitates counted in a gamma counter Osteocalcin values were reported in fmole/100 1, which was then converted to pmole/ml medium (3-day production) by dividing those values by 100. Values were expressed as the mean±S.E.M. of triplicate determinations for 5–6 wells for each condition. Each experiment was confirmed at least two times using cells from different calvarial preparations.

EXAMPLE 5

Effect of Trm and RLMP on Mineralization In Vitro

There was little apparent effect of either the sense or antisense oligonucleotides on the overall production of bone nodules in the non-stimulated cell culture system. When ROBs were stimulated with Trm, however, the antisense oligonucleotide to RLMP inhibited mineralization of nodules by >95%. The addition of exogenous BMP-6 to the oligonucleotide-treated cultures did not rescue the mineralization of RLMP-antisense-treated nodules.

Osteocalcin has long been synonymous with bone mineralization, and osteocalcin levels have been correlated with nodule production and mineralization. The RLMP-antisense oligonucleotide significantly decreases osteocalcin production, but the nodule count in antisense-treated cultures does not change significantly. In this case, the addition of exogenous BMP-6 only rescued the production of osteocalcin in RLMP-antisense-treated cultures by 10–15%. This suggests that the action of RLMP is downstream of, and more specific than, BMP-6.

EXAMPLE 6

Harvest and Purification of RNA

Cellular RNA from duplicate wells of ROBs (prepared according to Examples 1 and 2 in 6-well culture dishes) was harvested using 4M guanidine isothiocyanate (GIT) solution to yield statistical triplicates. Briefly, culture supernatant was aspirated from the wells, which were then overlayed with 0.6 ml of GIT solution per duplicate well harvest. After adding the GIT solution, the plates were swirled for 5–10 seconds (being as consistent as possible). Samples were saved at −70° C. for up to 7 days before further processing.

RNA was purified by a slight modification of standard methods according to Sambrook et al., *Molecular Cloning: a Laboratory Manual*, 2nd Ed., chapter 7.19, Cold Spring Harbor Press (1989). Briefly, thawed samples received 60 l 2.0 M sodium acetate (pH 4.0), 550 l phenol (water saturated) and 150 l chloroform:isoamyl alcohol (49:1). After vortexing, the samples were centrifuged (10000×g; 20 minutes; 4° C.), the aqueous phase transferred to a fresh tube, 600 l isopropanol was added and the RNA precipitated overnight at −20° C.

Following the overnight incubation, the samples were centrifuged (10000×g; 20 minutes) and the supernatant was aspirated gently. The pellets were resuspended in 400 l DEPC-treated water, extracted once with phenol:chloroform (1:1), extracted with chloroform:isoamyl alcohol (24:1) and precipitated overnight at −20° C. after addition of 40 l sodium acetate (3.0 M; pH 5.2) and 1.0 ml absolute ethanol. To recover the cellular RNA, the samples were centrifuged (10000×g; 20 min), washed once with 70% ethanol, air dried for 5–10 minutes and resuspended in 20 l of DEPC-treated water. RNA concentrations were calculated from optical densities that were determined with a spectrophotometer.

EXAMPLE 7

Reverse Transcription-Polymerase Chain Reaction

Heated total RNA (5 g in 10.5 l total volume DEPC-H$_2$O at 65° C. for 5 minutes) was added to tubes containing 4 l 5× MMLV-RT buffer, 2 l dNTPs, 2 l dT17 primer (10 pmol/ml), 0.5 l RNAsin (40 U/ml) and 1 l MMLV-RT (200 units/l). The samples were incubated at 37° C. for 1 hour, then at 95° C. for 5 minutes to inactivate the MMLV-RT. The samples were diluted by addition of 80 l of water.

Reverse-transcribed samples (5 l) were subjected to polymerase-chain reaction using standard methodologies (50 l total volume). Briefly, samples were added to tubes containing water and appropriate amounts of PCR buffer, 25 mM MgCl$_2$, dNTPs, forward and reverse primers for glyceraldehyde 3-phosphate dehydrogenase (GAP, a housekeeping gene) and/or BMP-6), $^{32}$P-dCTP, and Taq polymerase. Unless otherwise noted, primers were standardized to run consistently at 22 cycles (94° C., 30"; 58° C., 30"; 72° C., 20").

EXAMPLE 8

Quantitation of RT-PCR Products by Polyacrylamide Gel Electrophoresis (PAGE) and Phosphorimager Analysis RT-PCR products received 5 l/tube loading dye, were mixed, heated at 65° C. for 10 min and centrifuged. Ten l of each reaction was subjected to PAGE (12% polyacrylamide: bis; 15 V/well; constant current) under standard conditions. Gels were then incubated in gel preserving buffer (10% v/v glycerol, 7% v/v acetic acid, 40% v/v methanol, 43% deionized water) for 30 minutes, dried (80° C.) in vacuo for 1–2 hours and developed with an electronically-enhanced phosphoresence imaging system for 6–24 hours. Visualized bands were analyzed. Counts per band were plotted graphically.

EXAMPLE 9

Differential Display PCR

RNA was extracted from cells stimulated with glucocorticoid (Trm, 1 nM). Heated, DNase-treated total RNA (5 g in 10.5 l total volume in DEPC-H$_2$O at 65° C. for 5 minutes) was reverse transcribed as described in Example 7, but H-T$_{11}$M (SEQ ID. NO: 4) was used as the MMLV-RT primer. The resulting cDNAs were PCR-amplified as described above, but with various commercial primer sets (for example, H-T$_{11}$G (SEQ ID NO: 4) and H-AP-10 (SEQ ID. NO: 5); GenHunter Corp, Nashville, Tenn.). Radiolabelled PCR products were fractionated by gel electrophoresis on a DNA sequencing gel. After electrophoresis, the resulting gels were dried in vacuo and autoradiographs were exposed overnight. Bands representing differentially-expressed cDNAs were excised from the gel and reamplified by PCR using the method of Conner et al., *Proc. Natl. Acad. Sci. USA*, 88:278 (1983). The products of PCR reamplification were cloned into the vector PCR-II (TA cloning kit; InVitrogen, Carlsbad, Calif.).

EXAMPLE 10

Screening of a UMR 106 Rat Osteosarcoma Cell cDNA Library

A UMR 106 library (2.5×10$^{10}$ pfu/ml) was plated at 5×10$^4$ pfu/ml onto agar plates (LB bottom agar) and the plates were incubated overnight at 37° C. Filter membranes were overlaid onto plates for two minutes. Once removed, the filters were denatured, rinsed, dried and UV cross-linked. The filters were then incubated in pre-hyridization buffer (2× PIPES [pH 6.5], 5% formamide, 1% SDS and 100 g/ml denatured salmon sperm DNA) for 2 h at 42° C. A 260 base-pair radiolabelled probe (SEQ ID NO: 3; $^{32}$P labelled by random priming) was added to the entire hybridization mix/filters, followed by hybridization for 18 hours at 42° C. The membranes were washed once at room temperature (10 min, 1×SSC, 0.1% SDS) and three times at 55° C. (15 min, 0.1×SSC, 0.1% SDS).

After they were washed, the membranes were analyzed by autoradiography as described above. Positive clones were plaque purified. The procedure was repeated with a second filter for four minutes to minimize spurious positives. Plaque-purified clones were rescued as lambda SK(−) phagemids. Cloned cDNAs were sequenced as described below.

EXAMPLE 11

Sequencing of Clones

Cloned cDNA inserts were sequenced by standard methods. Ausubel et al., *Current Protocols in Molecular Biology*, Wiley Interscience (1988). Briefly, appropriate concentrations of termination mixture, template and reaction mixture were subjected to an appropriate cycling protocol (95° C., 30 s; 68° C., 30 s; 72° C., 60 s; ×25). Stop mixture was added to terminate the sequencing reactions. After heating at 92° C. for 3 minutes, the samples were loaded onto a denaturing 6% polyacrylamide sequencing gel (29:1 acrylamide:bis-acrylamide). Samples were electrophoresed for about 4 hours at 60 volts, constant current. After electrophoresis, the gels were dried in vacuo and autoradiographed.

The autoradiographs were analyzed manually. The resulting sequences were screened against the databases maintained by the National Center for Biotechnology Information (NIH, Bethesda, Md.; http://www.ncbi.nlm.nih.gov/) using the BLASTn program set with default parameters. Based on the sequence data, new sequencing primers were prepared and the process was repeated until the entire gene had been sequenced. All sequences were confirmed a minimum of three times in both orientations.

Nucleotide and amino acid sequences were also analyzed using the PCGENE software package (version 16.0). Percent homology values for nucleotide sequences were calculated by the program NALIGN, using the following parameters: weight of non-matching nucleotides, 10; weight of non-matching gaps, 10; maximum number of nucleotides considered, 50; and minimum number of nucleotides considered, 50.

For amino acid sequences, percent homology values were calculated using PALIGN. A value of 10 was selected for both the open gap cost and the unit gap cost.

EXAMPLE 12

Cloning of RLMP cDNA

The differential display PCR amplification products described in Example 9 contained a major band of approximately 260 base pairs. This sequence was used to screen a rat osteosarcoma (UMR 106) cDNA library. Positive clones were subjected to nested primer analysis to obtain the primer sequences necessary for amplifying the full length cDNA. (SEQ. ID NOs: 11, 12, 29, 30 and 31) One of those positive clones selected for further study was designated clone 10-4.

Sequence analysis of the full-length cDNA in clone 10-4, determined by nested primer analysis, showed that clone 10-4 contained the original 260 base-pair fragment identified by differential display PCR. Clone 10-4 (1696 base pairs; SEQ ID NO: 2) contains an open reading frame of 1371 base pairs encoding a protein having 457 amino acids (SEQ ID NO: 1). The termination codon, TGA, occurs at nucleotides 1444–1446. The polyadenylation signal at nucleotides 1675–1680, and adjacent poly(A)$^+$ tail, was present in the 3' noncoding region. There were two potential N-glycosylation sites, Asn-Lys-Thr and Asn-Arg-Thr, at amino acid positions 113–116 and 257–259 in SEQ ID NO: 1, respectively. Two potential cAMP- and cGMP-dependent protein kinase phosphorylation sites, Ser and Thr, were found at amino acid positions 191 and 349, respectively. There were five potential protein kinase C phosphorylation sites, Ser or Thr, at amino acid positions 3, 115, 166, 219, 442. One potential ATP/GTP binding site motif A (P-loop), Gly-Gly-Ser-Asn-Asn-Gly-Lys-Thr, was determined at amino acid positions 272–279.

In addition, two highly conserved putative LIM domains were found at amino acid positions 341–391 and 400–451. The putative LIM domains in this newly identified rat cDNA clone showed considerable homology with the LIM domains of other known LIM proteins. However, the overall homology with other rat LIM proteins was less than 25%. RLMP (also designated 10-4) has 78.5% amino acid homology to the human enigma protein (see U.S. Pat. No. 5,504,192), but only 24.5% and 22.7% amino acid homology to its closest rat homologs, CLP-36 and RIT-18, respectively.

EXAMPLE 13

Northern Blot Analysis of RLMP Expression

Thirty g of total RNA from ROBs, prepared according to Examples 1 and 2, was size fractionated by formaldehyde gel electrophoresis in 1% agarose flatbed gels and osmotically transblotted to nylon membranes. The blot was probed with a 600 base pair EcoR1 fragment of full-length 10-4 cDNA labeled with $^{32}$P-dCTP by random priming.

Northern blot analysis showed a 1.7 kb mRNA species that hybridized with the RLMP probe. RLMP mRNA was up-regulated approximately 3.7-fold in ROBs after 24 hours exposure to BMP-6. No up-regulation of RMLP expression was seen in BMP-2 or BMP-4-stimulated ROBs at 24 hours.

EXAMPLE 14

Statistical Methods

For each reported nodule/osteocalcin result, data from 5–6 wells from a representative experiment were used to calculate the mean±S.E.M. Graphs may be shown with data normalized to the maximum value for each parameter to allow simultaneous graphing of nodule counts, mineralized areas and osteocalcin.

For each reported RT-PCR, RNase protection assay or Western blot analysis, data from triplicate samples of representative experiments, were used to determine the mean±S.E.M. Graphs may be shown normalized to either day 0 or negative controls and expressed as fold-increase above control values.

Statistical significance was evaluated using a one-way analysis of variance with post-hoc multiple comparison corrections of Bonferroni as appropriate. D. V. Huntsberger, "The Analysis of Variance," in *Elements of Statistical Variance*, P. Billingsley (ed.), pp. 298–330, Allyn & Bacon Inc., Boston, Mass. (1977) and Sigmastat, Jandel Scientific, Corte Madera, Calif. Alpha levels for significance were defined as $p<0.05$.

EXAMPLE 15

Detection of Rat LIM Mineralization Protein by Western Blot Analysis

Polyclonal antibodies were prepared according to the methods of England et al., *Biochim. Biophys. Acta*, 623:171 (1980) and Timmer et al., *J. Biol. Chem.*, 268:24863 (1993).

HeLa cells were transfected with pCMV2/RLMP. Protein was harvested from the transfected cells according to the method of Hair et al., *Leukemia Research*, 20:1 (1996). Western Blot Analysis of native RLMP was performed as described by Towbin et al., *Proc. Natl. Acad. Sci. USA*, 76:4350 (1979).

EXAMPLE 16

Synthesis of the Rat LMP-Unique (RLMPU) Derived Human PCR Product

Based on the sequence of the rat LMP-1 cDNA, forward and reverse PCR primers (SEQ ID NOs: 15 and 16) were synthesized and a unique 223 base-pair sequence was PCR amplified from the rat LMP-1 cDNA. A similar PCR product was isolated from human MG63 osteosarcoma cell cDNA with the same PCR primers.

RNA was harvested from MG63 osteosarcoma cells grown in T-75 flasks. Culture supernatant was removed by aspiration and the flasks were overlayed with 3.0 ml of GIT solution per duplicate, swirled for 5–10 seconds, and the resulting solution was transferred to 1.5 ml eppendorf tubes (5 tubes with 0.6 ml/tube). RNA was purified by a slight modification of standard methods, for example, see Sambrook et al., *Molecular Cloning: A Laboratory Manual*, chapter 7, page 19, Cold Spring Harbor Laboratory Press (1989) and Boden et al., *Endocrinology*, 138:2820–28 (1997). Briefly, the 0.6 ml samples received 60 l 2.0 M sodium acetate (pH 4.0), 550 l water saturated phenol and 150 l chloroform:isoamyl alcohol (49:1). After addiiton of those reagents, the samples were vortexed, centrifuged (10000×. g; 20 min: 4 C.) and the aqueous phase transferred to a fresh tube. Isopropanol (600 l) was added and the RNA was precipitated overnight at −20° C. The samples were centrifuged (10000×g; 20 minutes) and the supernatant was aspirated gently. The pellets were resuspended in 400 l of DEPC-treated water, extracted once with phenol:chloroform (1:1), extracted with chloroform;isoamyl alcohol (24:1) and precipitated overnight at −20° C. in 40 l sodium acetate (3.0 M; pH 5.2) and 1.0 ml absolute ethanol. After precipitation, the samples were centrifuged (10000×g; 20 min), washed once with 70% ethanol, air dried for 5–10 minutes and resuspended in 20 l of DEPC-treated water. RNA concentrations were derived from optical densities.

Total RNA (5 g in 10.5 L total volume in DEPC-$H_2O$) was heated at 65° C. for 5 minutes, and then added to tubes containing 4 l 5× MMLV-RT buffer, 2 l dNTPs, 2 l dT17 primer (10 pmol/ml), 0.5 l RNAsin (40 U/ml) and 1 l MMLV-RT (200 units/l). The reactions were incubated at 37° C. for 1 hour. Afterward, the MMLV-RT was inactivated by heating at 95° C. for 5 minutes. The samples were diluted by addition of 80 L water.

Transcribed samples (5 l) were subjected to polymerase-chain reaction using standard methodologies (50 l total volume). Boden et al., *Endocrinology*, 138:2820–28 (1997); Ausubel et al., "Quantitation of rare DNAs by the polymerase chain reaction", in *Current Protocols in Molecular Biology*, chapter 15.31–1, Wiley & Sons, Trenton, N.J. (1990). Briefly, samples were added to tubes containing water and appropriate amounts of PCR buffer (25 mM $MgCl_2$, dNTPs, forward and reverse primers (for RLMPU; SEQ ID NOs: 15 and 16), $^{32}$P-dCTP, and DNA polymerase. Primers were designed to run consistently at 22 cycles for radioactive band detection and 33 cycles for amplification of PCR product for use as a screening probe (94° C., 30 sec, 58° C., 30 sec; 72° C., 20 sec).

Sequencing of the agarose gel-purified MG63 osteosarcoma-derived PCR product gave a sequence more than 95% homologous to the RLMPU PCR product. That sequence is designated HLMP unique region (HLMPU; SEQ ID NO: 6).

EXAMPLE 17

Screening of Reverse-Transcriptase-Derived MG63 cDNA

Screening was performed with PCR using specific primers (SEQ ID NOs: 16 and 17) as described in Example 7. A 717 base-pair MG63 PCR product was agarose gel purified and sequenced with the given primers (SEQ. ID NOs: 12, 15, 16, 17, 18, 27 and 28). Sequences were confirmed a minimum of two times in both directions. The MG63 sequences were aligned against each other and then against the full-length rat LMP cDNA sequence to obtain a partial human LMP cDNA sequence (SEQ ID NO: 7).

EXAMPLE 18

Screening of a Human Heart cDNA Library

Based on Northern blot experiments, it was determined that LMP-1 is expressed at different levels by several different tissues, including human heart muscle. A human heart cDNA library was therefore examined. The library was plated at $5 \times 10^4$ pfu/ml onto agar plates (LB bottom agar) and plates were grown overnight at 37° C. Filter membranes were overlaid onto the plates for two minutes. Afterward, the filters denatured, rinsed, dried, UV cross-linked and incubated in pre-hyridization buffer (2× PIPES [pH 6.5]; 5% formamide, 1% SDS, 100 g/ml denatured salmon sperm DNA) for 2 h at 42° C. A radiolabelled, LMP-unique, 223 base-pair probe ($^{32}$P, random primer labelling; SEQ ID NO: 6) was added and hybridized for 18 h at 42° C. Following hybridization, the membranes were washed once at room temperature (10 min, 1×SSC, 0.1% SDS) and three times at 55° C. (15 min, 0.1×SSC, 0.1% SDS). Double-positive plaque-purified heart library clones, identified by autoradiography, were rescued as lambda phagemids according to the manufacturers' protocols (Stratagene, La Jolla, Calif.).

Restriction digests of positive clones yielded cDNA inserts of varying sizes. Inserts greater than 600 base-pairs in length were selected for initial screening by sequencing. Those inserts were sequenced by standard methods as described in Example 11.

One clone, number 7, was also subjected to automated sequence analysis using primers corresponding to SEQ ID NOs: 11–14, 16 and 27. The sequences obtained by these methods were routinely 97–100% homologous. Clone 7 (Partial Human LMP-1 cDNA from a heart library; SEQ. ID NO: 8) contained sequence that was more than 87% homologous to the rat LMP cDNA sequence in the translated region.

EXAMPLE 19

Determination of Full-Length Human LMP-1 cDNA

Overlapping regions of the MG63 human osteosarcoma cell cDNA sequence and the human heart cDNA clone 7 sequence were used to align those two sequences and derive a complete human cDNA sequence of 1644 base-pairs. NALIGN, a program in the PCGENE software package, was used to align the two sequences. The overlapping regions of the two sequences constituted approximately 360 base-pairs having complete homology except for a single nucleotide substitution at nucleotide 672 in the MG63 cDNA (SEQ ID NO: 7) with clone 7 having an "A" instead of a "G" at the corresponding nucleotide 516 (SEQ ID NO: 8).

The two aligned sequences were joined using SEQIN, another subprogram of PCGENE, using the "G" substitution of the MG63 osteosarcoma cDNA clone. The resulting sequence is shown in SEQ ID NO: 9. Alignment of the novel human-derived sequence with the rat LMP-1 cDNA was accomplished with NALIGN. The full-length human LMP-1 cDNA sequence (SEQ. ID NO: 9) is 87.3% homologous to the translated portion of rat LMP-1 cDNA sequence.

EXAMPLE 20

Determination of Amino Acid Sequence of Human LMP-1

The putative amino acid sequence of human LMP-1 was determined with the PCGENE subprogram TRANSL. The open reading frame in SEQ ID NO: 9 encodes a protein comprising 457 amino acids (SEQ. ID NO: 10). Using the PCGENE subprogram Palign, the human LMP-1 amino acid sequence was found to be 94.1% homologous to the rat LMP-1 amino acid sequence.

EXAMPLE 21

Determination of the 5 Prime Untranslated Region of the Human LMP cDNA

MG63 5' cDNA was amplified by nested RT-PCR of MG63 total RNA using a 5' rapid amplification of cDNA ends (5' RACE) protocol. This method included first strand cDNA synthesis using a lock-docking oligo (dT) primer with two degenerate nucleotide positions at the 3' end (Chenchik et al., *CLONTECHniques. X:*5 (1995); Borson et al., *PC Methods Applic.,* 2:144 (1993)). Second-strand synthesis is performed according to the method of Gubler et al., *Gene,* 25:263 (1983), with a cocktail of *Escherichia coli* DNA polymerase I, RNase H, and *E. coli* DNA ligase. After creation of blunt ends with T4 DNA polymerase, double-stranded cDNA was ligated to the fragment (5'-CTAATAC-GACTCACTATAGGGCTCGAGCGGCCGC-CCGGGCAGGT-3') (SEQ. ID NO: 19). Prior to RACE, the adaptor-ligated cDNA was diluted to a concentration suitable for Marathon RACE reactions (1:50). Adaptor-ligated double-stranded cDNA was then ready to be specifically cloned.

First-round PCR was performed with the adaptor-specific oligonucleotide, 5'-CCATCCTAATACGACTCACTAT-AGGGC-3' (AP1) (SEQ. ID NO: 20) as sense primer and a Gene Specific Primer (GSP) from the unique region described in Example 16 (HLMPU). The second round of PCR was performed using a nested primers GSP1-HLMPU (antisense/reverse primer) (SEQ. ID NO: 23) and GSP2-HLMPUF (SEQ. ID NO: 24) (see Example 16; sense/forward primer). PCR was performed using a commercial kit (Advantage cDNA PCR core kit; CloneTech Laboratories Inc., Palo Alto, Calif.) that utilizes an antibody-mediated, but otherwise standard, hot-start protocol. PCR conditions for MG63 cDNA included an initial hot-start denaturation (94° C., 60 sec) followed by: 94° C., 30 sec; 60° C., 30 sec; 68° C., 4 min; 30 cycles. The first-round PCR product was approximately 750 base-pairs in length whereas the nested PCR product was approximately 230 base-pairs. The first-round PCR product was cloned into linearized pCR 2.1 vector (3.9 Kb). The inserts were sequenced in both directions using M13 Forward and Reverse primers (SEQ. ID NO: 11; SEQ. ID NO: 12)

EXAMPLE 22

Determination of Full-length Human LMP-1 cDNA with 5 Prime UTR

Overlapping MG63 human osteosarcoma cell cDNA 5'-UTR sequence (SEQ ID NO: 21), MG63 717 base-pair sequence (Example 17; SEQ ID NO: 8) and human heart cDNA clone 7 sequence (Example 18) were aligned to derive a novel human cDNA sequence of 1704 base-pairs (SEQ. ID NO: 22). The alignment was accomplished with NALIGN, (both PCGENE and Omiga 1.0; Intelligenetics). Over-lapping sequences constituted nearly the entire 717 base-pair region (Example 17) with 100% homology. Joining of the aligned sequences was accomplished with SEQIN.

EXAMPLE 23

Construction of LIM Protein Expression Vector

The construction of pHIS-5ATG LMP-1 s expression vector was carried out with the sequences described in Examples 17 and 18. The 717 base-pair clone (Example 17; SEQ ID NO: 7) was digested with ClaI and EcoRV. A small fragment (~250 base-pairs) was gel purified. Clone 7 (Example 18; SEQ ID NO: 8) was digested with ClaI and XbaI and a 1400 base-pair fragment was gel purified. The isolated 250 base-pair and 1400 base-pair restriction fragments were ligated to form a fragment of ~1650 base-pairs.

Due to the single nucleotide substitution in Clone 7 (relative to the 717 base-pair PCR sequence and the original rat sequence) a stop codon at translated base-pair 672 resulted. Because of this stop codon, a truncated (short) protein was encoded, hence the name LMP-1s. This was the construct used in the expression vector (SEQ ID NO: 32). The full length cDNA sequence with 5' UTR (SEQ ID NO: 33) was created by alignment of SEQ ID NO: 32 with the 5' RACE sequence (SEQ ID NO: 21). The amino acid sequence of LMP-1s (SEQ ID NO: 34) was then deduced as a 223 amino acid protein and confirmed by Western blot (as in Example 15) to run at the predicted molecular weight of ~23.7 kD.

The pHis-ATG vector (InVitrogen, Carlsbad, Calif.) was digested with EcoRV and XbaI. The vector was recovered and the 1650 base-pair restriction fragment was then ligated into the linearized pHis-ATG. The ligated product was cloned and amplified. The pHis-ATG-LMP-1s Expression vector, also designated pHIS-A with insert HLMP-1s, was purified by standard methods.

EXAMPLE 24

Induction of Bone Nodule Formation and Mineralization In Vitro with LMP Expression Vector Rat Calvarial cells were isolated and grown in secondary culture according to Example 1. Cultures were either unstimulated or stimulated with glucocorticoid (GC) as described in Example 1. A modification of the Superfect Reagent (Qiagen, Valencia, Calif.) transfection protocol was used to transfect 3 g/well of each vector into secondary rat calvarial osteoblast cultures according to Example 25.

Mineralized nodules were visualized by Von Kossa staining, as described in Example 3. Human LMP-1s gene product overexpression alone induced bone nodule formation (~203 nodules/well) in vitro. Levels of nodules were approximately 50% of those induced by the GC positive control (~412 nodules/well). Other positive controls included the pHisA-LMP-Rat expression vector (~152 nodules/well) and the pCMV2/LMP-Rat-Fwd Expression vector (~206 nodules/well), whereas the negative controls included the pCMV2/LMP-Rat-Rev. Expression vector (~2 nodules/well) and untreated (NT) plates (~4 nodules/well). These data demonstrate that the human cDNA was at least as osteoinductive as the rat cDNA. The effect was less than that observed with GC stimulation, most likely due to suboptimal doses of Expression vector.

EXAMPLE 25

LMP-Induced Cell Differentiation In Vitro and In Vivo

The rat LMP cDNA in clone 10-4 (see Example 12) was excised from the vector by double-digesting the clone with NotI and ApaI overnight at 37° C. Vector pCMV2 MCS (InVitrogen, Carlsbad, Calif.) was digested with the same restriction enzymes. Both the linear cDNA fragment from clone 10-4 and pCMV2 were gel purified, extracted and ligated with T4 ligase. The ligated DNA was gel purified, extracted and used to transform E. coli JM 109 cells for amplification. Positive agar colonies were picked, digested with NotI and ApaI and the restriction digests were examined by gel electrophoresis. Stock cultures were prepared of positive clones.

A reverse vector was prepared in analogous fashion except that the restriction enzymes used were XbaI and HindIII. Because these restriction enzymes were used, the LMP cDNA fragment from clone 10-4 was inserted into pRc/CMV2 in the reverse (that is, non-translatable) orientation. The recombinant vector produced is designated pCMV2/RLMP.

An appropriate volume of pCMV 10-4 (60 nM final concentration is optimal [3 g]; for this experiment a range of 0–600 nM/well [0–30 g/well] final concentration is preferred) was resuspended in Minimal Eagle Media (MEM) to 450 l final volume and vortexed for 10 seconds. Superfect was added (7.5 l/ml final solution), the solution was vortexed for 10 seconds and then incubated at room termperature for 10 minutes. Following this incubation, MEM supplemented with 10% FBS (1 ml/well; 6 ml/plate) was added and mixed by pipetting.

The resulting solution was then promptly pipetted (1 ml/well) onto washed ROB cultures. The cultures were incubated for 2 hours at 37° C. in a humidified atmosphere containing 5% $CO_2$. Afterward, the cells were gently washed once with sterile PBS and the appropriate normal incubation medium was added.

Results demonstrated significant bone nodule formation in all rat cell cultures which were induced with pCMV10-4. For example, pCMV10-4 transfected cells produced 429 nodules/well. Positive control cultures, which were exposed to Trm, produced 460 nodules/well. In contrast, negative controls, which received no treatment, produced 1 nodule/well. Similarly, when cultures were transfected with pCMV10-4 (reverse), no nodules were observed.

For demonstrating de novo bone formation in vivo, marrow was aspirated from the hindlimbs of 4–5 week old normal rats (rnu/+; heterozygous for recessive athymic condition). The aspirated marrow cells were washed in alpha MEM, centrifuged, and RBCs were lysed by resuspending the pellet in 0.83% $NH_4Cl$ in 10 mM Tris (pH 7.4). The remaining marrow cells were washed 3× with MEM and transfected for 2 hours with 9 g of pCMV-LMP-1s (forward or reverse orientation) per $3\times10^6$ cells. The transfected cells were then washed 2× with MEM and resuspended at a concentration of $3\times10^7$ cells/ml.

The cell suspension (100 l) was applied via sterile pipette to a sterile 2×5 mm type I bovine collagen disc (Sulzer Orthopaedics, Wheat Ridge, Colo.). The discs were surgically implanted subcutaneously on the skull, chest, abdomen or dorsal spine of 4–5 week old athymic rats (rnu/rnu). The animals were scarified at 3–4 weeks, at which time the discs or surgical areas were excised and fixed in 70% ethanol. The fixed specimens were analyzed by radiography and undecalcified histologic examination was performed on 5 m thick sections stained with Goldner Trichrome. Experiments were also performed using devitalized (guanidine extracted) demineralized bone matrix (Osteotech, Shrewsbury, N.J.) in place of collagen discs.

Radiography revealed a high level of mineralized bone formation that conformed to the form of the original collagen disc containing LMP-1s transfected marrow cells. No mineralized bone formation was observed in the negative control (cells transfected with a reverse-oriented version of the LMP-1s cDNA that did not code for a translated protein), and absorption of the carrier appeared to be well underway.

Histology revealed new bone trabeculae lined with osteoblasts in the LMP-1s transfected implants. No bone was seen along with partial resorption of the carrier in the negative controls.

Radiography of a further experiment in which 18 sets (9 negative control pCMV-LMP-REV & 9 experimental pCMV-LMP-1s) of implants were added to sites alternating between lumbar and thoracic spine in athymic rats demonstrated 0/9 negative control implants exhibiting bone formation (spine fusion) between vertebrae. All nine of the pCMV-LMP-1 s treated implants exhibited solid bone fusions between vertebrae.

EXAMPLE 26

The Synthesis of pHIS-5' ATG LMP-1s Expression Vector from the Sequences Demonstrated in Examples 2 and 3

The 717 base-pair clone (Example 17) was digested with ClaI and EcoRV (New England Biologicals, city, MA). A small fragment (~250 base-pairs) was gel purified. Clone No. 7 (Example 18) was digested with ClaI and XbaI. A 1400 base-pair fragment was gel purified from that digest. The isolated 250 base-pair and 1400 base-pair cDNA fragments were ligated by standard methods to form a fragment of ~1650 bp. The pHis-A vector (InVitrogen) was digested with EcoRV and XbaI. The linearized vector was recovered and ligated to the chimeric 1650 base-pair cDNA fragment. The ligated product was cloned and amplified by standard methods, and the pHis-A- 5' ATG LMP-1 s expression vector, also denominated as the vector pHis-A with insert HLMP-1 s, was deposited at the ATCC as previously described.

EXAMPLE 27

The Induction of Bone Nodule Formation and Mineralization In Vitro with pHis-5' ATG LMP-1s Expression Vector Rat calvarial cells were isolated and grown in secondary culture according to Example 1. Cultures were either unstimulated or stimulated with glucocorticoid (GC) according to Example 1. The cultures were transfected with 3 g of recombinant pHis-A vector DNA/well as described in Example 25. Mineralized nodules were visualized by Von Kossa staining according to Example 3.

Human LMP-1s gene product overexpression alone (i.e., without GC stimulation) induced significant bone nodule formation (~203 nodules/well) in vitro. This is approximately 50% of the amount of nodules produced by cells exposed to the GC positive control (~412 nodules/well). Similar results were obtained with cultures transfected with pHisA-LMP-Rat Expression vector (~152 nodules/well) and pCMV2/LMP-Rat-Fwd (~206 nodules/well). In contrast, the negative control pCMV2/LMP-Rat-Rev yielded (~2 nodules/well), while approximately 4 nodules/well were seen in the untreated plates. These data demonstrate that the human LMP-1 cDNA was at least as osteoinductive as the rat LMP-1 cDNA in this model system. The effect in this experiment was less than that observed with GC stimulation; but in some the effect was comparable.

EXAMPLE 28

LMP Induces Secretion of a Soluble Osteoinductive Factor

Overexpression of RLMP-1 or HLMP-1 s in rat calvarial osteoblast cultures as described in Example 24 resulted in significantly greater nodule formation than was observed in the negative control. To study the mechanism of action of LIM mineralization protein conditioned medium was harvested at different time points, concentrated to 10×, sterile filtered, diluted to its original concentration in medium containing fresh serum, and applied for four days to untransfected cells.

Conditioned media harvested from cells transfected with RLMP-1 or HLMP-1s at day 4 was approximately as effective in inducing nodule formation as direct overexpression of RLMP-1 in transfected cells. Conditioned media from cells transfected with RLMP-1 or HLMP-1 in the reverse orientation had no apparent effect on nodule formation. Nor did conditioned media harvested from LMP-1 transfected cultures before day 4 induce nodule formation. These data suggest that expression of LMP-1 caused the synthesis and/or secretion of a soluble factor, which did not appear in culture medium in effectie amounts until 4 days post transfection.

Since overexpression of rLMP-1 resulted in the secretion of an osteoinductive factor into the medium, Western blot analysis was used to determine if LM P-1 protein was present in the medium. The presence of rLMP-1 protein was assessed using antibody specific for LMP-1 (QDPDEE) and detected by conventional means. LMP-1 protein was found only in the cell layer of the culture and not detected in the medium.

Partial purification of the osteoinductive soluble factor was accomplished by standard 25% and 100% ammonium sulfate cuts followed by DE-52 anion exchange batch chromatography (100 mM or 500 mM NaCl). All activity was observed in the high ammonium sulfate, high NaCl fractions. Such localization is consistent with the possibility of a single factor being responsible for conditioning the medium.

EXAMPLE 29

Gene Therapy in Lumbar Spine Fusion Mediated by Low Dose Adenovirus

This study determined the optimal dose of adenoviral delivery of the LMP-1 cDNA (SEQ ID NO: 2) to promote spine fusion in normal, that is, immune competent, rabbits.

A replication-deficient human recombinant adenovirus was constructed with the LMP-1 cDNA (SEQ ID NO: 2) driven by a CMV promoter using the Adeno-Quest™ Kit (Quantum Biotechnologies, Inc., Montreal). A commercially available (Quantum Biotechnologies, Inc., Montreal) recombinant adenovirus containing the beta-galactosidase gene was used as a control.

Initially, an in vitro dose response experiment was performed to determine the optimal concentration of adenovirus-delivered LMP-1 ("AdV-LMP-1") to induce bone differentiation in rat calvarial osteoblast cultures using a 60-minute transduction with a multiplicity of infection ("MOI") of 0.025, 0.25, 2.5, or 25 plaque-forming units (pfu) of virus per cell. Positive control cultures were differentiated by a 7-day exposure to $10^9$ M glucocorticoid ("GC"). Negative control cultures were left untreated. On day 14, the number of mineralized bone nodules was counted after von Kossa staining of the cultures, and the level of osteocalcin secreted into the medium (pmol/mL) was measured by radioimmunoassay (mean±SEM).

The results of this experiment are shown in Table I. Essentially no spontaneous nodules formed in the untreated negative control cultures. The data show that a MOI equal to 0.25 pfu/cell is most effective for osteoinducing bone nodules, achieving a level comparable to the positive control (GC). Lower and higher doses of adenovirus were less effective.

TABLE I

| Outcome | Neg. Ctrl. | GC | AdV-LMP-1 Dose (MOI) | | | |
|---|---|---|---|---|---|---|
| | | | 0.025 | 0.25 | 2.5 | 25 |
| Bone Nodules | 0.5 ± 0.2 | 188 ± 35 | 79.8 ± 13 | 145.1 ± 13 | 26.4 ± 15 | 87.6 ± 2 |
| Osteocalcin | 1.0 ± 0.1 | 57.8 ± 9 | 28.6 ± 11 | 22.8 ± 1 | 18.3 ± 3 | 26.0 ± 2 |

In vivo experiments were then performed to determine if the optimal in vitro dose was capable of promoting inter-transverse process spine fusions in skeletally mature New Zealand white rabbits. Nine rabbits were anesthetized and 3 cc of bone marrow was aspirated from the distal femur through the intercondylar notch using an 18 gauge needle. The buffy coat was then isolated, a 10-minute transduction with AdV-LMP-1 was performed, and the cells were returned to the operating room for implantation. Single level posterolateral lumbar spine arthrodesis was performed with decortication of transverse processes and insertion of carrier (either rabbit devitalized bone matrix or a collagen sponge) containing 8–15 million autologous nucleated buffy coat cells transduced with either AdV-LMP-1 (MOI=0.4) or AdV-BGal (MOI=0.4). Rabbits were euthanized after 5 weeks and spine fusions were assessed by manual palpation, plain x-rays, CT scans, and undecalcified histology.

The spine fusion sites that received AdV-LMP-1 induced solid, continuous spine fusion masses in all nine rabbits. In contrast, the sites receiving AdV-BGal, or a lower dose of AdV-LMP-1 (MOI=0.04) made little or no bone and resulted in spine fusion at a rate comparable to the carrier alone (<40%). These results were consistent as evaluated by manual palpation, CT scan, and histology. Plain radiographs, however, sometimes overestimated the amount of bone that was present, especially in the control sites. LMP-1 cDNA delivery and bone induction was successful with both of the carrier materials tested. There was no evidence of systemic or local immune response to the adenovirus vector.

These data demonstrate consistent bone induction in a previously validated rabbit spine fusion model which is quite challenging. Furthermore, the protocol of using autogenous bone marrow cells with intraoperative ex vivo gene transduction (10 minutes) is a more clinically feasible procedure than other methods that call for overnight transduction or cell expansion for weeks in culture. In addition, the most effective dose of recombinant adenovirus (MOI=0.25) was substantially lower than doses reported in other gene therapy applications (MOI-40-500). We believe this is due to the fact that LMP-1 is an intracellular signaling molecule and may have powerful signal amplification cascades. Moreover, the observation that the same concentration of AdV-LMP-1 that induced bone in cell culture was effective in vivo was also surprising given the usual required increase in dose of other growth factors when translating from cell culture to animal experiments. Taken together, these observations indicate that local gene therapy using adenovirus to deliver the LMP-1 cDNA is possible and the low dose required will likely minimize the negative effects of immune response to the adenovirus vector.

EXAMPLE 30

Use of Peripheral Venous Blood Nucleated Cells (Buffy Coat) for Gene Therapy with LMP-1 cDNA To Make Bone In four rabbits we performed spine fusion surgery as above (Example 29) except the transduced cells were the buffy coat from venous blood rather than bone marrow. These cells were transfected with Adeno-LMP or pHIS-LMP plasmid and had equivalent successful results as when bone marrow cells were used. This discovery of using ordinary venous blood cells for gene delivery makes gene therapy more feasible clinically since it avoids painful marrow harvest under general anesthesia and yields two times more cells per mL of starting material.

EXAMPLE 31

Isolation of Human LMP-1 Splice Variants

Intron/Exon mRNA transcript splice variants are a relatively common regulatory mechanism in signal transduction and cellular/tissue development. Splice variants of various genes have been shown to alter protein—protein, protein-DNA, protein-RNA, and protein-substrate interactions. Splice variants may also control tissue specificity for gene expression allowing different forms (and therefore functions) to be expressed in various tissues. Splice variants are a common regulatory phenomenon in cells. It is possible that the LMP splice variants may result in effects in other tissues such as nerve regeneration, muscle regeneration, or development of other tissues.

To screen a human heart cDNA library for splice variants of the HLMP-1 sequence, a pair of PCR primer corresponding to sections of SEQ ID NO: 22 was prepared. The forward PCR primer, which was synthesized using standard techniques, corresponds to nucleotides 35–54 of SEQ ID NO: 22. It has the following sequence:

```
5' GAGCCGGCATCATGGATTCC 3'    (SEQ ID NO: 35)
```

The reverse PCR primer, which is the reverse complement of nucleotides 820–839 in SEQ ID NO: 22, has the following sequence:

```
5' GGTGCCTGCACAATGGAGGT 3'    (SEQ ID NO: 36)
```

The forward and reverse PCR primers were used to screen human heart cDNA (Clon Tech, Cat No. 7404-1) for sequences similar to HLMP-1 by standard techniques, using a cycling protocol of 94° C. for 30 seconds, 64° C. for 30 seconds, and 72° C. for 1 minute, repeated 30 times and followed by a 10 minute incubation at 72° C. The amplification cDNA sequences were gel-purified and submitted to the Emory DNA Sequence Core Facility for sequencing. The clones were sequenced using standard techniques and the sequences were examined with PCGENE (Intelligenetics; Programs SEQUIN and NALIGN) to determine homology to SEQ ID NO: 22. Two homologous nucleotide sequences with putative alternative splice sites compared to SEQ ID NO: 22 were then translated to their respective protein products with Intelligenetic's program TRANSL.

One of these two novel human cDNA sequences (SEQ ID NO: 37) comprises 1456 bp:

```
         10         20         30         40         50         60
CGACGCAGAG CAGCGCCCTG GCCGGGCCAA GCAGGAGCCG GCATCATGGA TTCCTTCAAG 70         80         90        100        110        120
GTAGTGCTGG AGGGGCCAGC ACCTTGGGGC TTCCGGCTGC AAGGGGGCAA GGACTTCAAT 130        140        150        160        170        180
GTGCCCCTCT CCATTTCCCG GCTCACTCCT GGGGGCAAAG CGGCGCAGGC CGGAGTGGCC 190        200        210        220        230        240
GTGGGTGACT GGGTGCTGAG CATCGATGGC GAGAATGCGG GTAGCCTCAC ACACATCGAA 250        260        270        280        290        300
GCTCAGAACA AGATCCGGGC CTGCGGGGAG CGCCTCAGCC TGGGCCTCAG CAGGGCCCAG 310        320      *  330        340    *   350        360
CCGGTTCAGA GCAAACCGCA GAAGGTGCAG ACCCCTGACA AACAGCCGCT CCGACCGCTG 370        380        390        400        410        420
GTCCCAGATG CCAGCAAGCA GCGGCTGATG GAGAACACAG AGGACTGGCG GCCGCGGCCG 430        440        450        460        470        480
GGGACAGGCC AGTCGCGTTC CTTCCGCATC CTTGCCCACC TCACAGGCAC CGAGTTCATG 490        500        510        520        530        540
CAAGACCCGG ATGAGGAGCA CCTGAAGAAA TCAAGCCAGG TGCCCAGGAC AGAAGCCCCA 550        560        570        580        590        600
GCCCCAGCCT CATCTACACC CCAGGAGCCC TGGCCTGGCC CTACCGCCCC CAGCCCTACC 610        620        630        640        650        660
AGCCGCCCGC CCTGGGCTGT GGACCCTGCG TTTGCCGAGC GCTATGCCCC GGACAAAACG 670        680        690        700        710        720
AGCACAGTGC TGACCCGGCA CAGCCAGCCG GCCACGCCCA CGCCGCTGCA GAGCCGCACC 730        740        750        760        770        780
TCCATTGTGC AGGCAGCTGC CGGAGGGGTG CCAGGAGGGG GCAGCAACAA CGGCAAGACT 790        800        810        820        830        840
CCCGTGTGTC ACCAGTGCCA CAAGGTCATC CGGGGCCGCT ACCTGGTGGC GTTGGGCCAC 850        860        870        880        890        900
GCGTACCACC CGGAGGAGTT TGTGTGTAGC CAGTGTGGGA AGGTCCTGGA AGAGGGTGGC 910        920        930        940        950        960
TTCTTTGAGG AGAAGGGCGC CATCTTCTGC CCACCATGCT ATGACGTGCG CTATGCACCC 970        980        990       1000       1010       1020
AGCTGTGCCA AGTGCAAGAA GAAGATTACA GGCGAGATCA TGCACGCCCT GAAGATGACC 1030       1040       1050       1060       1070       1080
TGGCACGTGC ACTGCTTTAC CTGTGCTGCC TGCAAGACGC CCATCCGGAA CAGGGCCTTC 1090       1100       1110       1120       1130       1140
TACATGGAGG AGGGCGTGCC CTATTGCGAG CGAGACTATG AGAAGATGTT TGGCACGAAA 1150       1160       1170       1180       1190       1200
TGCCATGGCT GTGACTTCAA GATCGACGCT GGGGACCGCT TCCTGGAGGC CCTGGGCTTC 1210       1220       1230       1240       1250       1260
AGCTGGCATG ACACCTGCTT CGTCTGTGCG ATATGTCAGA TCAACCTGGA AGCAAAGACC 1270       1280       1290       1300       1310       1320
TTCTACTCCA AGAAGGACAG GCCTCTCTGC AAGAGCCATG CCTTCTCTCA TGTGTGAGCC 1330       1340       1350       1360       1370       1380
CCTTCTGCCC ACAGCTGCCG CGGTGGCCCC TAGCCTGAGG GGCCTGGAGT CGTGGCCCTG 1390       1400       1410       1420       1430       1440
CATTTCTGGG TAGGGCTGGC AATGGTTGCC TTAACCCTGG CTCCTGGCCC GAGCCTGGGC

1450
TCCCGGGCCC TGCCCA
```

Reading frame shifts caused by the deletion of a 119 bp fragment (between *) and the addition of a 17 bp fragment (underlined) results in a truncated gene product having the following derived amino acid sequence (SEQ ID NO: 38):

```
         10         20         30         40         50         60
MDSFKVVLEG PAPWGFRLQG GKDFNVPLSI SRLTPGGKAA QAGVAVGDWV LSIDGENAGS 70         80         90        100        110        120
LTHIEAQNKI RACGERLSLG LSRAQPVQNK PQKVQTPDKQ PLRPLVPDAS KQRLMENTED 130        140        150        160        170        180
WRPRPGTGQS RSFRILAHLT GTEFMQDPDE EHLKKSSQVP RTEAPAPASS TPQEPWPGPT 190        200        210        220        230        240
APSPTSRPPW AVDPAFAERY APDKTSTVLT RHSQPATPTP LQSRTSIVQA AAGGVPGGGS 250        260        270        280        290        300
NNGKTPVCHQ CHQVIRARYL VALGHAYHPE EFVCSQCGKV LEEGGFFEEK GAIFCPPCYD 310        320        330        340        350        360
VRYAPSCAKC KKKITGEIMH ALKMTWHVLC FTCAACKTPI RNRAFYMEEG VPYCERDYEK 370        380        390        400        410        420
MFGTKCQWCD FKIDAGDRFL EALGFSWHDT CFVCAICQIN LEGKTFYSKK DRPLCKSHAF

SHV
```

This 423 amino acid protein demonstrates 100% homology to the protein shown in Sequence ID No. 10, except for the sequence in the highlighted area (amino acids 94–99), which are due to the nucleotide changes depicted above.

The second novel human heart cDNA sequence (SEQ ID NO: 39) comprises 1575 bp:

```
         10         20         30         40         50         60
CGACGCAGAG CAGCGCCCTG GCCGGGCCAA GCAGGAGCCG GCATCATGGA TTCCTTCAAG 70         80         90        100        110        120
GTAGTGCTGG AGGGGCCAGC ACCTTGGGGC TTCCGGCTGC AAGGGGGCAA GGACTTCAAT 130        140        150        160        170        180
GTGCCCCTCT CCATTTCCCG GCTCACTCCT GGGGGCAAAG CGGCGCAGGC CGGAGTGGCC 190        200        210        220        230        240
GTGGGTGACT GGGTGCTGAG CATCGATGGC GAGAATGCGG GTAGCCTCAC ACACATCGAA 250        260        270        280        290        300
GCTCAGAACA AGATCCGGGC CTGCGGGGAG CGCCTCAGCC TGGGCCTCAG CAGGGCCCAG 310        320        330        340        350        360
CCGGTTCAGA GCAAACCGCA GAAGGCCTCC GCCCCCGCCG CGGACCCTCC GCGGTACACC 370        380        390        400        410        420
TTTGCACCCA GCGTCTCCCT CAACAAGACG GCCCGGCCCT TTGGGGCGCC CCCGCCCGCT 430        440        450        460        470        480
GACAGCGCCC CGCAACAGAA TGGGTGCAGA CCCCTGACAA ACAGCCGCTC CGACCGCTGG 490        500        510        520        530        540
TCCCAGATGC CAGCAAGCAG CGGCTGATGG AGAACACAGA GGACTGGCGG CCGCGGCCGG 550        560        570        580        590        600
GGACAGGCCA GTCGCGTTCC TTCCGCATCC TTGCCCACCT CACAGGCACC GAGTTCATGC 610        620        630        640        650        660
AAGACCCGGA TGAGGAGCAC CTGAAGAAAT CAAGCCAGGT GCCCAGGACA GAAGCCCCAG 670        680        690        700        710        720
CCCCAGCCTC ATCTACACCC CAGGAGCCCT GGCCTGGCCC TACCGCCCCC AGCCCTACCA 730        740        750        760        770        780
GCCGCCCGCC CTGGGCTGTG GACCCTGCGT TTGCCGAGCG CTATGCCCCG GACAAAACGA 790        800        810        820        830        840
GCACAGTGCT GACCCGGCAC AGCCAGCCGG CCACGCCCAC GCCGCTGCAG AGCCGCACCT 850        860        870        880        890        900
CCATTGTGCA GGCAGCTGCC GGAGGGGTGC CAGGAGGGGG CAGCAACAAC GGCAAGACTC
```

```
             910        920        930        940        950        960
        CCGTGTGTCA CCAGTGCCAC AAGGTCATCC GGGGCCGCTA CCTGGTGGCG TTGGGCCACG 970        980        990       1000       1010       1020
        CGTACCACCC GGAGGAGTTT GTGTGTAGCC AGTGTGGGAA GGTCCTGGAA GAGGGTGGCT 1030       1040       1050       1060       1070       1080
        TCTTTGAGGA GAAGGGCGCC ATCTTCTGCC CACCATGCTA TGACGTGCGC TATGCACCCA 1090       1100       1110       1120       1130       1140
        GCTGTGCCAA GTGCAAGAAG AAGATTACAG GCGAGATCAT GCACGCCCTG AAGATGACCT 1150       1160       1170       1180       1190       1200
        GGCACGTGCA CTGCTTTACC TGTGCTGCCT GCAAGACGCC CATCCGGAAC AGGGCCTTCT 1210       1220       1230       1240       1250       1260
        ACATGGAGGA GGGCGTGCCC TATTGCGAGC GAGACTATGA GAAGATGTTT GGCACGAAAT 1270       1280       1290       1300       1310       1320
        GCCATGGCTG TGACTTCAAG ATCGACGCTG GGGACCGCTT CCTGGAGGCC CTGGGCTTCA 1330       1340       1350       1360       1370       1380
        GCTGGCATGA CACCTGCTTC GTCTGTGCGA TATGTCAGAT CAACCTGGAA GGAAAGACCT 1390       1400       1410       1420       1430       1440
        TCTACTCCAA GAAGGACAGG CCTCTCTGCA AGAGCCATGC CTTCTCTCAT GTGTGAGCCC 1450       1460       1470       1480       1490       1500
        CTTCTGCCCA CAGCTGCCGC GGTGGCCCCT AGCCTGAGGG GCCTGGAGTC GTGGCCCTGC 1510       1520       1530       1540       1550       1560
        ATTTCTGGGT AGGGCTGGCA ATGGTTGCCT TAACCCTGGC TCCTGGCCCG AGCCTGGGCT

1570
        CCCGGGCCCT GCCCA
```

Reading frame shifts caused by the addition of a 17 bp fragment (bolded, italicized and underlined) results in an early translation stop codon at position 565–567 (underlined).

The derived amino acid sequence (SEQ ID NO: 40) consists of 153 amino acids:

```
        10         20         30         40         50         60
MDSFKVVLEG PAPWGFRLQG GKDFNVPLSI SRLTPGGKAA QAGVAVGDWV LSIDGENAGS 70         80         90        100        110        120
LTHIEAQNKI RACGERLSLG LSRAQPVQSK PQKASAPAAD PPRYTFAPSV SLNKTARPFG 130        140        150
APPPADSAPQ QNGCRPLTNS RSDRWSQMPA SSG
```

This protein demonstrates 100% homology to SEQ ID NO: 10 until amino acid 94, where the addition of the 17 bp fragment depicted in the nucleotide sequence results in a frame shift. Over amino acids 94–153, the protein is not homologous to SEQ ID NO: 10. Amino acids 154–457 in SEQ ID NO: 10 are not present due to the early stop codon depicted in nucleotide sequence.

EXAMPLE 32

Genomic HLMP-1 Nucleotide Sequence

Applicants have identified the genomic DNA sequence encoding HLMP-1, including putative regulatory elements associated with HLMP-1 expression. The entire genomic sequence is shown in SEQ ID. NO: 41. This sequence was derived from AC023788 (clone RP11-564G9), Genome Sequencing Center, Washington University School of Medicine, St. Louis, Mo.

The putative promoter region for HLMP-1 spans nucleotides 2,660–8,733 in SEQ ID NO: 41. This region comprises, among other things, at least ten potential glucocorticoid response elements ("GREs") (nucleotides 6148–6153, 6226–6231, 6247–6252, 6336–6341, 6510–6515, 6552–6557, 6727–6732, 6752–6757, 7738–7743, and 8255–8260), twelve potential Sma-2 homologues to Mothers against *Drosophilla* decapentaplegic ("SMAD") binding element sites (nucleotides 3569–3575, 4552–4558, 4582–4588, 5226–5232, 6228–6234, 6649–6655, 6725–6731, 6930–6936, 7379–7384, 7738–7742, 8073–8079, and 8378–8384), and three TATA boxes (nucleotides 5910–5913, 6932–6935, and 7380–7383). The three TATA boxes, all of the GREs, and eight of the SMAD binding elements ("SBEs") are grouped in the region spanning nucleotides 5,841–8,733 in SEQ ID NO: 41. These regulatory elements can be used, for example, to regulate expression of exogenous nucleotide sequences encoding proteins involved in the process of bone formation. This would permit systemic administration of therapeutic factors or genes relating to bone formation and repair, as well as factors or genes associated with tissue differentiation and development.

In addition to the putative regulatory elements, 13 exons corresponding to the nucleotide sequence encoding HLMP-1 have been identified. These exons span the following nucleotides in SEQ ID NO: 41:

| Exon 1 | 8733–8767 |
| Exon 2 | 9790–9895 |
| Exon 3 | 13635–13787 |
| Exon 4 | 13877–13907 |
| Exon 5 | 14387–14502 |
| Exon 6 | 15161–15297 |
| Exon 7 | 15401–15437 |
| Exon 8 | 16483–16545 |
| Exon 9 | 16689–16923 |
| Exon 10 | 18068–18248 |
| Exon 11 | 22117–22240 |
| Exon 12 | 22323–22440 |
| Exon 13 | 22575–22911 |

In HLMP-2 there is another exon (Exon 5A), which spans nucleotides 14887–14904.

All cited publications and patents are hereby incorporated by reference in their entirety.

While the foregoing specification teaches the principles of the present invention, with examples provided for the purpose of illustration, it will be appreciated by one skilled in the art from reading this disclosure that various changes in form and detail can be made without departing from the true scope of the invention.

We claim:

1. An isolated human LIM mineralization protein (LMP) encoded by SEQ ID NO: 37 or SEQ ID NO: 39.

2. An isolated human LIM mineralization protein (LMP) comprising an amino acid sequence selected from the group consisting of SEQ ID NO: 38 and SEQ ID NO: 40.

3. An in vitro method of manufacturing the protein of claim 2, said method comprising transfecting isolated host cells with an expression vector comprising the nucleic acid sequence of SEQ ID NO: 37 or SEQ ID NO: 39, whereby said protein is expressed.

* * * * *

SEQUENCE LISTING

```
<160> NUMBER OF SEQ ID NOS: 42

<210> SEQ ID NO 1
<211> LENGTH: 457
<212> TYPE: PRT
<213> ORGANISM: Rattus norvegicus

<400> SEQUENCE: 1

Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Ala Gln Ser Lys Pro Gln Lys Ala Leu Thr
                 85                  90                  95

Pro Pro Ala Asp Pro Pro Arg Tyr Thr Phe Ala Pro Ser Ala Ser Leu
            100                 105                 110

Asn Lys Thr Ala Arg Pro Phe Gly Ala Pro Pro Pro Thr Asp Ser Ala
        115                 120                 125

Leu Ser Gln Asn Gly Gln Leu Leu Arg Gln Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu Phe Met Lys Lys Ser Ser Gln
            180                 185                 190

Val Pro Arg Thr Glu Ala Pro Ala Pro Ala Ser Thr Ile Pro Gln Glu
        195                 200                 205

Ser Trp Pro Gly Pro Thr Thr Pro Ser Pro Thr Ser Arg Pro Pro Trp
    210                 215                 220
```

```
Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
            245                 250                 255

Asn Arg Thr Ser Ile Val Gln Ala Ala Gly Gly Gly Thr Gly Gly
        260                 265                 270

Gly Ser Asn Asn Gly Lys Thr Pro Val Cys His Gln Cys His Lys Ile
        275                 280                 285

Ile Arg Gly Arg Tyr Leu Val Ala Leu Gly His Ala Tyr His Pro Glu
        290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Ser Cys Tyr Asp Val Arg
                325                 330                 335

Tyr Ala Pro Ser Cys Ala Lys Cys Lys Lys Ile Thr Gly Glu Ile
            340                 345                 350

Met His Ala Leu Lys Met Thr Trp His Val Pro Cys Phe Thr Cys Ala
        355                 360                 365

Ala Cys Lys Thr Pro Ile Arg Asn Arg Ala Phe Tyr Met Glu Glu Gly
370                 375                 380

Ala Pro Tyr Cys Glu Arg Asp Tyr Glu Lys Met Phe Gly Thr Lys Cys
385                 390                 395                 400

Arg Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Asp Lys Pro Leu
        435                 440                 445

Cys Lys Ser His Ala Phe Ser His Val
    450                 455

<210> SEQ ID NO 2
<211> LENGTH: 1696
<212> TYPE: DNA
<213> ORGANISM: Rattus norvegicus

<400> SEQUENCE: 2
gcacgaggat cccagcgcgg ctcctggagg ccgccaggca gccgcccagc cgggcattca      60
ggagcaggta ccatggattc cttcaaggta gtgctggagg acctgccccc ttggggcttc     120
cgtctgcaag ggggcaagga cttcaacgtg cccctctcca tctctcggct cactcctgga     180
ggcaaggccg cacaggccgg tgtggccgtg ggagactggg tactgagtat cgacggtgag     240
aacgccggaa gcctcacaca cattgaagcc cagaacaaga tccgtgcctg tggggagcgc     300
ctcagcctgg tcttagcaga gcccagcct gctcagagca aaccacagaa ggccctgacc     360
cctcccgccg accccccgag gtacactttt gcaccaagcg cctccctcaa caagacggcc     420
cggcccttcg gggcaccccc acctactgac agcgccctgt cgcagaatgg acagctgctc     480
agacagctgg tccctgatgc cagcaagcag cggctgatga gaatactga agactggcgc     540 ccgcggccag ggacaggcca gtcccgttcc ttccgcatcc ttgctcacct cacgggcaca     600
gagttcatgc aagacccgga tgaggaattc atgaagaagt caagccaggt gcccaggaca     660
gaagccccag cccagcctc aaccataccc aggaatcct ggcctggccc caccacccc      720 agccccacca gccgcccacc ctgggccgta gatcctgcat tgctgagcg ctatgcccca     780
```

| | |
|---|---|
| gacaaaacca gcacagtgct gacccgacac agccagccag ccacacctac gcctctgcag | 840 |
| aaccgcacct ccatagttca ggctgcagct ggaggggggca caggaggagg cagcaacaat | 900 |
| ggcaagacgc ctgtatgcca ccagtgccac aagatcatcc gcggccgata cctggtagca | 960 |
| ctgggccacg cgtaccatcc tgaggaattt gtgtgcagcc agtgtgggaa ggtcctggaa | 1020 |
| gagggtggct tcttcgagga aagggagct atcttttgcc cctcctgcta tgatgtgcgc | 1080 |
| tatgcaccca gctgtgccaa atgcaagaag aagatcactg gagagatcat gcatgcgctg | 1140 |
| aagatgacct ggcatgttcc ctgcttcacc tgtgcagcct gcaaaacccc tatccgcaac | 1200 |
| agggctttct acatggagga gggggctccc tactgcgagc gagattacga aaagatgtttt | 1260 |
| ggcacaaagt gtcgcggctg tgacttcaag atcgatgccg gggaccgttt cctggaagcc | 1320 |
| ctgggtttca gctggcatga tacgtgtttt gtttgcgcaa tatgtcaaat caacttggaa | 1380 |
| ggaaagacct tctactccaa gaaggacaag cccctgtgca agagccatgc cttttcccac | 1440 |
| gtatgagcac ctcctcacac tactgccacc ctactctgcc agaagggtga taaaatgaga | 1500 |
| gagctctctc tccctcgacc tttctgggtg gggctggcag ccattgtcct agccttggct | 1560 |
| cctggccaga tcctggggct ccctcctcac agtccccttt cccacacttc ctccaccacc | 1620 |
| accaccgtca ctcacaggtg ctagcctcct agccccagtt cactctggtg tcacaataaa | 1680 |
| cctgtatgta gctgtg | 1696 |

<210> SEQ ID NO 3
<211> LENGTH: 260
<212> TYPE: DNA
<213> ORGANISM: Rattus norvegicus

<400> SEQUENCE: 3

| | |
|---|---|
| ttctacatgg aggaggggc tccctactgc gagcgagatt acgagaagat gtttggcaca | 60 |
| aagtgtcgcg gctgtgactt caagatcgat gccggggacc gtttcctgga agccctgggt | 120 |
| ttcagctggc atgatacgtg ttttgtttgc gcaatatgtc aaatcaactt ggaaggaaag | 180 |
| accttctact ccaagaagga caagcccctg tgcaagagcc atgccttttc ccacgtatga | 240 |
| gcacctcctc acactactgc | 260 |

<210> SEQ ID NO 4
<211> LENGTH: 16
<212> TYPE: DNA
<213> ORGANISM: MMLV

<400> SEQUENCE: 4

| | |
|---|---|
| aagctttttt tttttg | 16 |

<210> SEQ ID NO 5
<211> LENGTH: 13
<212> TYPE: DNA
<213> ORGANISM: MMLV

<400> SEQUENCE: 5

| | |
|---|---|
| aagcttggct atg | 13 |

<210> SEQ ID NO 6
<211> LENGTH: 223
<212> TYPE: DNA
<213> ORGANISM: Homo sapiens

<400> SEQUENCE: 6

| | |
|---|---|
| atccttgctc acctcacggg caccgagttc atgcaagacc cggatgagga gcacctgaag | 60 |

```
aaatcaagcc aggtgcccag gacagaagcc ccagccccag cctcatctac accccaggag    120
ccctggcctg gccctaccgc ccccagccct accagccgcc cgccctgggc tgtggaccct    180
gcgtttgccg agcgctatgc cccagacaaa accagcacag tgc                     223

<210> SEQ ID NO 7
<211> LENGTH: 717
<212> TYPE: DNA
<213> ORGANISM: Homo sapiens

<400> SEQUENCE: 7
atggattcct tcaaggtagt gctggagggg ccagcacctt ggggcttccg gctgcaaggg     60
ggcaaggact tcaatgtgcc cctctccatt tcccggctca ctcctggggg caaagcggcg    120
caggccggag tggccgtggg tgactgggtg ctgagcatcg atggcgagaa tgcgggtagc    180
ctcacacaca tcgaagctca gaacaagatc cgggcctgcg gggagcgcct cagcctgggc    240
ctcagcaggg cccagccggt tcagagcaaa ccgcagaagg cctccgcccc cgccgcggac    300
cctccgcggt acacctttgc acccagcgtc tccctcaaca agacgcccg  gcccttggg    360 gcgcccccgc ccgctgacag cgccccgcaa cagaatggac agccgctccg accgctggtc    420
ccagatgcca gcaagcagcg gctgatggag aacacagagg actggcggcc gcggccgggg    480
acaggccagt cgcgttcctt ccgcatcctt gcccactca caggcaccga gttcatgcaa    540
gacccggatg aggagcacct gaagaaatca agccaggtgc ccaggacaga agccccagcc    600
ccagcctcat ctacaccccca ggagccctgg cctggcccta ccgccccag ccctaccagc    660 cgcccgccct gggctgtgga ccctgcgttt gccgagcgct atgccccgga caaaacg      717

<210> SEQ ID NO 8
<211> LENGTH: 1488
<212> TYPE: DNA
<213> ORGANISM: Homo sapiens

<400> SEQUENCE: 8
atcgatggcg agaatgcggg tagcctcaca cacatcgaag ctcagaacaa gatccgggcc     60
tgcggggagc gcctcagcct gggcctcagc agggcccagc cggttcagag caaaccgcag    120
aaggcctccg cccccgccgc ggaccctccg cggtacacct ttgcacccag cgtctccctc    180
aacaagacgg cccggccctt ggggcgcccc cgcccgctg acagcgcccc gcaacagaat    240
ggacagccgc tccgaccgct ggtcccagat gccagcaagc agcggctgat ggagaacaca    300
gaggactggc ggccgcggcc ggggacaggc cagtcgcgtt ccttccgcat ccttgcccac    360
ctcacaggca ccgagttcat gcaagacccg gatgaggagc acctgaagaa atcaagccag    420
gtgcccagga cagaagcccc agccccagcc tcatctacac cccaggagcc ctggcctggc    480
cctaccgccc ccagccctac cagccgcccg ccctgagctg tggaccctgc gtttgccgag    540
cgctatgccc cggacaaaac gagcacagtg ctgacccggc acagccagcc ggccacgccc    600
acgccgctgc agagccgcac ctccattgtg caggcagctg ccggaggggt gccaggaggg    660
ggcagcaaca acggcaagac tcccgtgtgt caccagtgcc acaaggtcat ccggggccgc    720
tacctggtgg cgttgggcca cgcgtaccac ccggaggagt ttgtgtgtag ccagtgtggg    780
aaggtcctgg aagagggtgg cttctttgag gagaagggcc ccatcttctg cccaccatgc    840
tatgacgtgc gctatgcacc cagctgtgcc aagtgcaaga agaagattac aggcgagatc    900
atgcacgccc tgaagatgac ctggcacgtg cactgcttta cctgtgctgc ctgcaagacg    960
```

| | |
|---|---|
| cccatccgga acagggcctt ctacatggag gagggcgtgc cctattgcga gcgagactat | 1020 |
| gagaagatgt ttggcacgaa atgccatggc tgtgacttca agatcgacgc tggggaccgc | 1080 |
| ttcctggagg ccctgggctt cagctggcat gacacctgct tcgtctgtgc gatatgtcag | 1140 |
| atcaacctgg aaggaaagac cttctactcc aagaaggaca ggcctctctg caagagccat | 1200 |
| gccttctctc atgtgtgagc cccttctgcc cacagctgcc gcggtggccc ctagcctgag | 1260 |
| gggcctggag tcgtggccct gcatttctgg gtagggctgg caatggttgc cttaaccctg | 1320 |
| gctcctggcc cgagcctggg ctcccgggcc cctgcccacc caccttatcc tcccacccca | 1380 |
| ctccctccac caccacagca caccggtgct ggccacacca gccccctttc acctccagtg | 1440 |
| ccacaataaa cctgtaccca gctgaattcc aaaaaatcca aaaaaaaa | 1488 |

<210> SEQ ID NO 9
<211> LENGTH: 1644
<212> TYPE: DNA
<213> ORGANISM: Homo sapiens

<400> SEQUENCE: 9

| | |
|---|---|
| atggattcct tcaaggtagt gctggagggg ccagcacctt ggggcttccg gctgcaaggg | 60 |
| ggcaaggact tcaatgtgcc cctctccatt tcccggctca ctcctggggg caaagcggcg | 120 |
| caggccggag tggccgtggg tgactgggtg ctgagcatcg atggcgagaa tgcgggtagc | 180 |
| ctcacacaca tcgaagctca gaacaagatc cgggcctgcg gggagcgcct cagcctgggc | 240 |
| ctcagcaggg cccagccggt tcagagcaaa ccgcagaagg cctccgcccc cgccgcggac | 300 |
| cctccgcggt acacctttgc acccagcgtc tccctcaaca agacggcccg gccctttggg | 360 |
| gcgcccccgc ccgctgacag cgccccgcaa cagaatggac agccgctccg accgctggtc | 420 |
| ccagatgcca gcaagcagcg gctgatggag aacacagagg actggcggcc gcggccgggg | 480 |
| acaggccagt cgcgttcctt ccgcatcctt gcccacctca caggcaccga gttcatgcaa | 540 |
| gacccggatg aggagcacct gaagaaatca agccaggtgc ccaggacaga agccccagcc | 600 |
| ccagcctcat ctacacccca ggagccctgg cctggcccta ccgccccag ccctaccagc | 660 |
| cgcccgccct gggctgtgga ccctgcgttt gccgagcgct atgccccgga caaaacgagc | 720 |
| acagtgctga cccggcacag ccagccggcc acgcccacgc cgctgcagag ccgcacctcc | 780 |
| attgtgcagg cagctgccgg aggggtgcca ggaggggca gcaacaacgg caagactccc | 840 |
| gtgtgtcacc agtgccacaa ggtcatccgg ggccgctacc tggtggcgtt gggccacgcg | 900 |
| taccacccgg aggagtttgt gtgtagccag tgtgggaagg tcctggaaga gggtggcttc | 960 |
| tttgaggaga agggcgccat cttctgccca ccatgctatg acgtcgcta tgcacccagc | 1020 |
| tgtgccaagt gcaagaagaa gattacaggc gagatcatgc acgccctgaa gatgacctgg | 1080 |
| cacgtgcact gctttacctg tgctgcctgc aagacgccca tccggaacag ggccttctac | 1140 |
| atggaggagg gcgtgcccta ttgcgagcga ctatgagaga gatgtttgg cacgaaatgc | 1200 |
| catggctgtg acttcaagat cgacgctggg accgcttcc tggaggccct gggcttcagc | 1260 |
| tggcatgaca cctgcttcgt ctgtgcgata tgtcagatca acctggaagg aaagaccttc | 1320 |
| tactccaaga aggacaggcc tctctgcaag agccatgcct ctctcatgt gtgagcccct | 1380 |
| tctgcccaca gctgccgcgg tggccccctag cctgaggggc ctggagtcgt ggccctgcat | 1440 |
| ttctgggtag ggctggcaat ggttgcctta accctggctc ctggcccgag cctgggctcc | 1500 |
| cgggcccctg cccacccacc ttatcctccc accccactcc ctccaccacc acagcacacc | 1560 |
| ggtgctggcc acaccagccc cctttcacct ccagtgccac aataaacctg tacccagctg | 1620 | aattccaaaa aatccaaaaa aaaa                                                                          1644

<210> SEQ ID NO 10
<211> LENGTH: 457
<212> TYPE: PRT
<213> ORGANISM: Homo sapiens

<400> SEQUENCE: 10

Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Gly Val Pro Gly Gly
            260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
            340                 345                 350

Met His Ala Leu Lys Met Thr Trp His Val His Cys Phe Thr Cys Ala
        355                 360                 365

```
Ala Cys Lys Thr Pro Ile Arg Asn Arg Ala Phe Tyr Met Glu Glu Gly
        370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
        435                 440                 445

Cys Lys Ser His Ala Phe Ser His Val
        450                 455
```

<210> SEQ ID NO 11
<211> LENGTH: 22
<212> TYPE: DNA
<213> ORGANISM: Rattus norvegicus

<400> SEQUENCE: 11
gccagggttt tcccagtcac ga                                              22

<210> SEQ ID NO 12
<211> LENGTH: 22
<212> TYPE: DNA
<213> ORGANISM: Rattus norvegicus

<400> SEQUENCE: 12
gccagggttt tcccagtcac ga                                              22

<210> SEQ ID NO 13
<211> LENGTH: 22
<212> TYPE: DNA
<213> ORGANISM: Homo sapiens

<400> SEQUENCE: 13
tcttagcaga gcccagcctg ct                                              22

<210> SEQ ID NO 14
<211> LENGTH: 22
<212> TYPE: DNA
<213> ORGANISM: Homo sapiens

<400> SEQUENCE: 14
gcatgaactc tgtgcccgtg ag                                              22

<210> SEQ ID NO 15
<211> LENGTH: 20
<212> TYPE: DNA
<213> ORGANISM: Rattus norvegicus

<400> SEQUENCE: 15
atccttgctc acctcacggg                                                 20

<210> SEQ ID NO 16
<211> LENGTH: 22
<212> TYPE: DNA
<213> ORGANISM: Rattus norvegicus

<400> SEQUENCE: 16
gcactgtgct ggttttgtct gg                                              22

<210> SEQ ID NO 17
<211> LENGTH: 23
<212> TYPE: DNA
<213> ORGANISM: Homo sapiens

<400> SEQUENCE: 17
catggattcc ttcaaggtag tgc                                         23

<210> SEQ ID NO 18
<211> LENGTH: 20
<212> TYPE: DNA
<213> ORGANISM: Homo sapiens

<400> SEQUENCE: 18
gttttgtctg gggcagagcg                                             20

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: adaptor
      for Marathon RACE reactions

<400> SEQUENCE: 19
ctaatacgac tcactatagg gctcgagcgg ccgcccgggc aggt                  44

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: PCR primer
      specific for Marathon RACE adaptor

<400> SEQUENCE: 20
ccatcctaat acgactcact atagggc                                     27

<210> SEQ ID NO 21
<211> LENGTH: 765
<212> TYPE: DNA
<213> ORGANISM: Homo sapiens

<400> SEQUENCE: 21
ccgttgtttg taaaacgacg cagagcagcg ccctggccgg gccaagcagg agccggcatc   60
atggattcct tcaaggtagt gctggagggg ccagcacctt ggggcttccg gctgcaaggg  120
ggcaaggact tcaatgtgcc ctcctccatt tcccggctca cctctggggg caaggccgtg  180
caggccggag tggccgtaag tgactgggtg ctgagcatcg atggcgagaa tgcgggtagc  240
ctcacacaca tcgaagctca gaacaagatc cgggcctgcg gggagcgcct cagcctgggc  300
ctcaacaggg cccagccggt tcagaacaaa ccgcaaaagg cctccgcccc cgccgcggac  360
cctccgcggt acacctttgc accaagcgtc tccctcaaca agacggcccg gcccttgggg  420
gcgcccccgc ccgctgacag cgccccgcag cagaatggac agccgctccg accgctggtc  480
ccagatgcca gcaagcagcg gctgatggag aacacagagg actggcggcc gcggccgggg  540
acaggccagt gccgttcctt tcgcatcctt gctcaccta caggcaccga gttcatgcaa  600
gacccggatg aggagcacct gaagaaatca gccaggtgc caggacaga agccccagcc  660
ccagcctcat ctacacccca ggagccctgg cctggcccta ccgccccag ccctaccagc  720
cgcccgccct gggctgtgga ccctgcgttt gccgagcgct atgcc                  765

<210> SEQ ID NO 22
<211> LENGTH: 1689
<212> TYPE: DNA
<213> ORGANISM: Homo sapiens

<400> SEQUENCE: 22

```
cgacgcagag cagcgccctg gccgggccaa gcaggagccg gcatcatgga ttccttcaag      60
gtagtgctgg aggggccagc accttggggc ttccggctgc aagggggcaa ggacttcaat     120
gtgcccctct ccatttcccg gctcactcct gggggcaaag cggcgcaggc cggagtggcc     180
gtgggtgact gggtgctgag catcgatggc gagaatgcgg gtagcctcac acacatcgaa     240
gctcagaaca agatccgggc ctgcggggag cgcctcagcc tgggcctcag cagggcccag     300
ccggttcaga gcaaaccgca gaaggcctcc gcccccgccg cggaccctcc gcggtacacc     360
tttgcaccca gcgtctccct caacaagacg gcccggccct ttggggcgcc ccgcccgct     420
gacagcgccc cgcaacagaa tggacagccg ctccgaccgc tggtcccaga tgccagcaag     480
cagcggctga tggagaacac agaggactgg cggccgcggc cggggacagg ccagtcgcgt     540
tccttccgca tccttgccca cctcacaggc accgagttca tgcaagaccc ggatgaggag     600
cacctgaaga aatcaagcca ggtgcccagg acagaagccc cagccccagc ctcatctaca     660
ccccaggagc cctggcctgg ccctaccgcc ccagcccta ccagccgccc gccctgggct      720
gtggaccctg cgtttgccga gcgctatgcc ccggacaaaa cgagcacagt gctgacccgg     780
cacagccagc cggccacgcc cacgccgctg cagagccgca cctccattgt gcaggcagct     840
gccggagggg tgccaggagg gggcagcaac aacggcaaga ctcccgtgtg tcaccagtgc     900
cacaaggtca tccggggccg ctacctggtg cgttgggcc acgcgtacca cccggaggag     960
tttgtgtgta gccagtgtgg gaaggtcctg gagagggtg gcttctttga ggagaagggc    1020
gccatcttct gcccaccatg ctatgacgtg cgctatgcac ccagctgtgc caagtgcaag    1080
aagaagatta caggcgagat catgcacgcc ctgaagatga cctggcacgt gcactgcttt    1140
acctgtgctg cctgcaagac gcccatccgg aacagggcct tctacatgga ggagggcgtg    1200
ccctattgcg agcgagacta tgagaagatg tttggcacga aatgccatgg ctgtgacttc    1260
aagatcgacg ctggggaccg cttcctggag gccctgggct tcagctggca tgacacctgc    1320
ttcgtctgtg cgatatgtca gatcaacctg gaaggaaaga ccttctactc caagaaggac    1380
aggcctctct gcaagagcca tgccttctct catgtgtgag ccccttctgc ccacagctgc    1440
cgcggtggcc cctagcctga ggggcctgga gtcgtggccc tgcatttctg ggtagggctg    1500
gcaatggttg ccttaaccct ggctcctggc ccgagcctgg gctcccggc cctgccccac     1560
ccaccttatc ctcccacccc actccctcca ccaccacagc acaccggtgc tggccacacc    1620
agccccttt cacctccagt gccacaataa acctgtaccc agctgaattc caaaaaatcc     1680
aaaaaaaaa                                                             1689
```

<210> SEQ ID NO 23
<211> LENGTH: 22
<212> TYPE: DNA
<213> ORGANISM: Homo sapiens

<400> SEQUENCE: 23

```
gcactgtgct cgttttgtcc gg                                                22
```

<210> SEQ ID NO 24

-continued

```
<211> LENGTH: 21
<212> TYPE: DNA
<213> ORGANISM: Homo sapiens

<400> SEQUENCE: 24
tccttgctca cctcacgggc a                                              21

<210> SEQ ID NO 25
<211> LENGTH: 30
<212> TYPE: DNA
<213> ORGANISM: Homo sapiens

<400> SEQUENCE: 25
tcctcatccg ggtcttgcat gaactcggtg                                     30

<210> SEQ ID NO 26
<211> LENGTH: 28
<212> TYPE: DNA
<213> ORGANISM: Homo sapiens

<400> SEQUENCE: 26
gcccccgccc gctgacagcg ccccgcaa                                       28

<210> SEQ ID NO 27
<211> LENGTH: 24
<212> TYPE: DNA
<213> ORGANISM: Homo sapiens

<400> SEQUENCE: 27
tccttgctca cctcacgggc accg                                           24

<210> SEQ ID NO 28
<211> LENGTH: 22
<212> TYPE: DNA
<213> ORGANISM: Homo sapiens

<400> SEQUENCE: 28
gtaatacgac tcactatagg gc                                             22

<210> SEQ ID NO 29
<211> LENGTH: 23
<212> TYPE: DNA
<213> ORGANISM: Rattus norvegicus

<400> SEQUENCE: 29
gcggctgatg gagaatactg aag                                            23

<210> SEQ ID NO 30
<211> LENGTH: 23
<212> TYPE: DNA
<213> ORGANISM: Rattus norvegicus

<400> SEQUENCE: 30
atcttgtggc actggtggca tac                                            23

<210> SEQ ID NO 31
<211> LENGTH: 22
<212> TYPE: DNA
<213> ORGANISM: Rattus norvegicus

<400> SEQUENCE: 31
tgtgtcgggt cagcactgtg ct                                             22
```

-continued

<210> SEQ ID NO 32
<211> LENGTH: 1620
<212> TYPE: DNA
<213> ORGANISM: Homo sapiens

<400> SEQUENCE: 32

| | | | | | |
|---|---|---|---|---|---|
| atggattcct | tcaaggtagt | gctggagggg | ccagcacctt | ggggcttccg | gctgcaaggg | 60 |
| ggcaaggact | tcaatgtgcc | cctctccatt | tcccggctca | ctcctggggg | caaagcggcg | 120 |
| caggccggag | tggccgtggg | tgactgggtg | ctgagcatcg | atggcgagaa | tgcgggtagc | 180 |
| ctcacacaca | tcgaagctca | gaacaagatc | cgggcctgcg | gggagcgcct | cagcctgggc | 240 |
| ctcagcaggg | cccagccggt | tcagagcaaa | ccgcagaagg | cctccgcccc | cgccgcggac | 300 |
| cctccgcggt | acacctttgc | acccagcgtc | tccctcaaca | agacgcccg | gcccttggg | 360 |
| gcgcccccgc | ccgctgacag | cgccccgcaa | cagaatggac | agccgctccg | accgctggtc | 420 |
| ccagatgcca | gcaagcagcg | gctgatggag | aacacagagg | actggcggcc | gcggccgggg | 480 |
| acaggccagt | cgcgttcctt | ccgcatcctt | gcccacctca | caggcaccga | gttcatgcaa | 540 |
| gacccggatg | aggagcacct | gaagaaatca | agccaggtgc | caggacaga | agccccagcc | 600 |
| ccagcctcat | ctacaccca | ggagccctgg | cctggccta | ccgcccccag | ccctaccagc | 660 |
| cgcccgccct | gagctgtgga | ccctgcgttt | gccgagcgct | atgccccgga | caaaacgagc | 720 |
| acagtgctga | cccggcacag | ccagccgcc | acgcccacgc | cgctgcagag | ccgcacctcc | 780 |
| attgtgcagg | cagctgccgg | aggggtgcca | ggagggggca | gcaacaacgg | caagactccc | 840 |
| gtgtgtcacc | agtgccacaa | ggtcatccgg | ggccgctacc | tggtggcgtt | gggccacgcg | 900 |
| taccacccgg | aggagtttgt | gtgtagccag | tgtgggaagg | tcctggaaga | gggtggcttc | 960 |
| tttgaggaga | agggcgccat | cttctgccca | ccatgctatg | acgtgcgcta | tgcacccagc | 1020 |
| tgtgccaagt | gcaagaagaa | gattacaggc | gagatcatgc | acgccctgaa | gatgacctgg | 1080 |
| cacgtgcact | gctttacctg | tgctgcctgc | aagacgccca | tccggaacag | ggccttctac | 1140 |
| atggaggagg | gcgtgcccta | ttgcgagcga | gactatgaga | gatgtttgg | cacgaaatgc | 1200 |
| catggctgtg | acttcaagat | cgacgctggg | gaccgcttcc | tggaggccct | gggcttcagc | 1260 |
| tggcatgaca | cctgcttcgt | ctgtgcgata | tgtcagatca | acctggaagg | aaagaccttc | 1320 |
| tactccaaga | aggacaggcc | tctctgcaag | agccatgcct | tctctcatgt | gtgagccct | 1380 |
| tctgcccaca | gctgccgcgg | tggccccccag | cctgaggggc | ctggagtcgt | ggccctgcat | 1440 |
| ttctgggtag | ggctggcaat | ggttgcctta | acctggctc | ctggcccgag | cctgggctcc | 1500 |
| cgggcccctg | cccaccccacc | ttatcctccc | accccactcc | ctccaccacc | acagcacacc | 1560 |
| ggtgctggcc | acaccagccc | cctttcacct | ccagtgccac | aataaacctg | tacccagctg | 1620 |

<210> SEQ ID NO 33
<211> LENGTH: 1665
<212> TYPE: DNA
<213> ORGANISM: Homo sapiens

<400> SEQUENCE: 33

| | | | | | |
|---|---|---|---|---|---|
| cgacgcagag | cagcgccctg | gccgggccaa | gcaggagccg | gcatcatgga | ttccttcaag | 60 |
| gtagtgctgg | aggggccagc | accttggggc | ttccggctgc | aaggggcaa | ggacttcaat | 120 |
| gtgccctct | ccatttcccg | gctcactcct | ggggcaaag | cggcgcaggc | cggagtggcc | 180 |
| gtgggtgact | gggtgctgag | catcgatgga | gagaatgcgg | gtagcctcac | acacatcgaa | 240 |
| gctcagaaca | agatccgggc | ctgcggggag | cgcctcagcc | tgggcctcag | cagggcccag | 300 |

-continued

```
ccggttcaga gcaaaccgca gaaggcctcc gccccgccg cggaccctcc gcggtacacc        360
tttgcaccca gcgtctccct caacaagacg gcccggccct tgggggcgcc ccgcccgct        420
gacagcgccc cgcaacagaa tggacagccg ctccgaccgc tggtcccaga tgccagcaag      480
cagcggctga tggagaacac agaggactgg cggccgcggc cggggacagg ccagtcgcgt      540
tccttccgca tccttgccca cctcacaggc accgagttca tgcaagaccc ggatgaggag      600
cacctgaaga aatcaagcca ggtgcccagg acagaagccc cagccccagc ctcatctaca      660
ccccaggagc cctggcctgg ccctaccgcc cccagcccta ccagccgccc gccctgagct      720
gtggaccctg cgtttgccga gcgctatgcc ccggacaaaa cgagcacagt gctgacccgg      780
cacagccagc cggccacgcc cacgccgctg cagagccgca cctccattgt gcaggcagct      840
gccggagggg tgccaggagg gggcagcaac aacggcaaga ctcccgtgtg tcaccagtgc      900
cacaaggtca tccggggccg ctacctggtg gcgttgggcc acgcgtacca cccggaggag      960
tttgtgtgta gccagtgtgg gaaggtcctg gaagagggtg gcttctttga ggagaagggc     1020
gccatcttct gcccaccatg ctatgacgtg cgctatgcac ccagctgtgc caagtgcaag     1080
aagaagatta caggcgagat catgcacgcc ctgaagatga cctggcacgt gcactgcttt     1140
acctgtgctg cctgcaagac gcccatccgg aacagggcct tctacatgga ggagggcgtg     1200
ccctattgcg agcgagacta tgagaagatg tttggcacga aatgccatgg ctgtgacttc     1260
aagatcgacg ctggggaccg cttcctggag gccctgggct tcagctggca tgacacctgc     1320
ttcgtctgtg cgatatgtca gatcaacctg gaaggaaaga ccttctactc caagaaggac     1380
aggcctctct gcaagagcca tgccttctct catgtgtgag ccccttctgc ccacagctgc     1440
cgcggtggcc cctagcctga ggggcctgga gtcgtggccc tgcatttctg ggtagggctg     1500
gcaatggttg ccttaaccct ggctcctggc ccgagcctgg gctcccgggc cctgcccac      1560
ccaccttatc ctcccacccc actccctcca ccaccacagc acaccggtgc tggccacacc      1620
agcccccttt cacctccagt gccacaataa acctgtaccc agctg                     1665
```

<210> SEQ ID NO 34
<211> LENGTH: 223
<212> TYPE: PRT
<213> ORGANISM: Homo sapiens

<400> SEQUENCE: 34

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Gln Pro Leu Arg Pro Leu Val Pro Asp Ala Ser
```

-continued

```
              130                 135                 140
Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro
    210                 215                 220
```

<210> SEQ ID NO 35
<211> LENGTH: 20
<212> TYPE: DNA
<213> ORGANISM: Homo sapiens

<400> SEQUENCE: 35
gagccggcat catggattcc                                          20

<210> SEQ ID NO 36
<211> LENGTH: 20
<212> TYPE: DNA
<213> ORGANISM: Homo sapiens

<400> SEQUENCE: 36
gctgcctgca caatggaggt                                          20

<210> SEQ ID NO 37
<211> LENGTH: 1456
<212> TYPE: DNA
<213> ORGANISM: Homo sapiens

<400> SEQUENCE: 37
cgacgcagag cagcgccctg ccgggccaa gcaggagccg gcatcatgga ttccttcaag      60
gtagtgctgg aggggccagc accttgggc ttccggctgc aagggggcaa ggacttcaat     120
gtgcccctct ccatttcccg gctcactcct ggggcaaag cggcgcaggc cggagtggcc     180
gtgggtgact gggtgctgag catcgatggc gagaatgcgg gtagcctcac acacatcgaa    240
gctcagaaca agatccgggc ctgcggggag cgcctcagcc tgggcctcag cagggcccag    300
ccggttcaga gcaaaccgca gaaggtgcag acccctgaca acagccgct ccgaccgctg     360
gtcccagatg ccagcaagca gcggctgatg gagaacacag aggactggcg gccgcggccg    420
gggacaggcc agtcgcgttc cttccgcatc cttgcccacc tcacaggcac cgagttcatg    480
caagacccgg atgaggagca cctgaagaaa tcaagccagg tgcccaggac agaagccccca   540
gcccagcct catctacacc caggagccc tggcctggcc ctaccgcccc cagcctacc       600
agccgcccgc cctgggctgt ggaccctgcg tttgccgagc gctatgcccc ggacaaaacg    660
agcacagtgc tgacccggca cagccagccg gccacgccca cgccgctgca gagccgcacc    720
tccattgtgc aggcagctgc cggaggggtg ccaggagggg gcagcaacaa cggcaagact    780
cccgtgtgtc accagtgcca caaggtcatc cggggccgct acctggtggc gttgggccac    840
gcgtaccacc cggaggagtt tgtgtgtagc cagtgtggga aggtcctgga agagggtggc    900
ttctttgagg agaagggcgc catcttctgc ccaccatgct atgacgtgcg ctatgcaccc    960
agctgtgcca agtgcaagaa gaagattaca ggcgagatca tgcacgccct gaagatgacc   1020
```

-continued

```
tggcacgtgc actgctttac ctgtgctgcc tgcaagacgc ccatccggaa cagggccttc      1080
tacatggagg agggcgtgcc ctattgcgag cgagactatg agaagatgtt tggcacgaaa      1140
tgccatggct gtgacttcaa gatcgacgct ggggaccgct tcctggaggc cctgggcttc      1200
agctggcatg acacctgctt cgtctgtgcg atatgtcaga tcaacctgga aggaaagacc      1260
ttctactcca agaaggacag gcctctctgc aagagccatg ccttctctca tgtgtgagcc      1320
ccttctgccc acagctgccg cggtggcccc tagcctgagg ggcctggagt cgtggccctg      1380
catttctggg tagggctggc aatggttgcc ttaaccctgg ctcctggccc gagcctgggc      1440
tcccgggccc tgccca                                                       1456
```

<210> SEQ ID NO 38
<211> LENGTH: 423
<212> TYPE: PRT
<213> ORGANISM: Homo sapiens

<400> SEQUENCE: 38

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Asn Lys Pro Gln Lys Val Gln Thr
                 85                  90                  95

Pro Asp Lys Gln Pro Leu Arg Pro Leu Val Pro Asp Ala Ser Lys Gln
            100                 105                 110

Arg Leu Met Glu Asn Thr Glu Asp Trp Arg Pro Arg Pro Gly Thr Gly
        115                 120                 125

Gln Ser Arg Ser Phe Arg Ile Leu Ala His Leu Thr Gly Thr Glu Phe
    130                 135                 140

Met Gln Asp Pro Asp Glu Glu His Leu Lys Lys Ser Ser Gln Val Pro
145                 150                 155                 160

Arg Thr Glu Ala Pro Ala Pro Ala Ser Ser Thr Pro Gln Glu Pro Trp
                165                 170                 175

Pro Gly Pro Thr Ala Pro Ser Pro Thr Ser Arg Pro Pro Trp Ala Val
            180                 185                 190

Asp Pro Ala Phe Ala Glu Arg Tyr Ala Pro Asp Lys Thr Ser Thr Val
        195                 200                 205

Leu Thr Arg His Ser Gln Pro Ala Thr Pro Thr Pro Leu Gln Ser Arg
    210                 215                 220

Thr Ser Ile Val Gln Ala Ala Ala Gly Val Pro Gly Gly Gly Ser
225                 230                 235                 240

Asn Asn Gly Lys Thr Pro Val Cys His Gln Cys His Gln Val Ile Arg
                245                 250                 255

Ala Arg Tyr Leu Val Ala Leu Gly His Ala Tyr His Pro Glu Glu Phe
            260                 265                 270

Val Cys Ser Gln Cys Gly Lys Val Leu Glu Glu Gly Gly Phe Phe Glu
        275                 280                 285

Glu Lys Gly Ala Ile Phe Cys Pro Pro Cys Tyr Asp Val Arg Tyr Ala
```

```
              290             295             300
Pro Ser Cys Ala Lys Cys Lys Lys Ile Thr Gly Glu Ile Met His
305                 310                 315                 320

Ala Leu Lys Met Thr Trp His Val Leu Cys Phe Thr Cys Ala Ala Cys
                325                 330                 335

Lys Thr Pro Ile Arg Asn Arg Ala Phe Tyr Met Glu Glu Gly Val Pro
            340                 345                 350

Tyr Cys Glu Arg Asp Tyr Glu Lys Met Phe Gly Thr Lys Cys Gln Trp
                355                 360                 365

Cys Asp Phe Lys Ile Asp Ala Gly Asp Arg Phe Leu Glu Ala Leu Gly
370                 375                 380

Phe Ser Trp His Asp Thr Cys Phe Val Cys Ala Ile Cys Gln Ile Asn
385                 390                 395                 400

Leu Glu Gly Lys Thr Phe Tyr Ser Lys Lys Asp Arg Pro Leu Cys Lys
            405                 410                 415

Ser His Ala Phe Ser His Val
            420

<210> SEQ ID NO 39
<211> LENGTH: 1575
<212> TYPE: DNA
<213> ORGANISM: Homo sapiens

<400> SEQUENCE: 39
cgacgcagag cagcgccctg gccgggccaa gcaggagccg gcatcatgga ttccttcaag      60
gtagtgctgg aggggccagc accttgggc ttccggctgc aagggggcaa ggacttcaat     120
gtgcccctct ccatttcccg gctcactcct ggggcaaag cggcgcaggc cggagtggcc     180
gtgggtgact gggtgctgag catcgatggc gagaatgcgg tagcctcac acacatcgaa     240
gctcagaaca agatccgggc ctgcggggag cgcctcagcc tgggcctcag cagggcccag     300
ccggttcaga gcaaaccgca gaaggcctcc gccccgccg cggaccctcc gcggtacacc     360
tttgcaccca gcgtctccct caacaagacg gcccggcccc ttggggcgcc ccgcccgct     420
gacagcgccc cgcaacagaa tgggtgcaga cccctgacaa acagccgctc cgaccgctgg     480
tcccagatgc agcaagcag cggctgatgg agaacacaga ggactggcgg ccgcggccgg     540
ggacaggcca gtcgcgttcc ttccgcatcc ttgcccacct cacaggcacc gagttcatgc     600
aagacccgga tgaggagcac ctgaagaaat caagccaggt gcccaggaca gaagccccag     660
ccccagcctc atctacaccc caggagccct ggcctggccc taccgccccc agccctacca     720
gccgcccgcc ctgggctgtg accctgcgt tgccgagcg ctatgcccg acaaaacga     780
gcacagtgct gacccggcac agccagccgg ccacgcccac gccgctgcag agccgcacct     840
ccattgtgca ggcagctgcc ggaggggtgc aggaggggg cagcaacaac ggcaagactc     900
ccgtgtgtca ccagtgccac aaggtcatcc ggggccgcta cctggtggcg ttgggccacg     960
cgtaccaccc ggaggagttt gtgtgtagcc agtgtgggaa ggtcctggaa gagggtggct    1020
tctttgagga aagggcgcc atcttctgcc caccatgcta tgacgtgcgc tatgcaccca    1080
gctgtgccaa gtgcaagaag aagattacag gcgagatcat gcacgccctg aagatgacct    1140
ggcacgtgca ctgctttacc tgtgctgcct gcaagacgcc catccggaac agggccttct    1200
acatggagga gggcgtgccc tattgcgagc gagactatga aagatgtttt ggcacgaaat    1260
gccatggctg tgacttcaag atcgacgctg ggaccgctt cctggaggcc ctgggcttca    1320
gctggcatga cacctgcttc gtctgtgcga tatgtcagat caacctggaa ggaaagacct    1380
```

-continued

```
tctactccaa gaaggacagg cctctctgca agagccatgc cttctctcat gtgtgagccc    1440
cttctgccca cagctgccgc ggtggcccct agcctgaggg gcctggagtc gtggccctgc    1500
atttctgggt agggctggca atggttgcct taaccctggc tcctggcccg agcctgggct    1560
cccgggccct gccca                                                    1575
```

<210> SEQ ID NO 40
<211> LENGTH: 153
<212> TYPE: PRT
<213> ORGANISM: Homo sapiens

<400> SEQUENCE: 40

```
Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
            115                 120                 125

Pro Gln Gln Asn Gly Cys Arg Pro Leu Thr Asn Ser Arg Ser Asp Arg
    130                 135                 140

Trp Ser Gln Met Pro Ala Ser Ser Gly
145                 150
```

<210> SEQ ID NO 41
<211> LENGTH: 24740
<212> TYPE: DNA
<213> ORGANISM: Homo sapiens
<220> FEATURE:
<221> NAME/KEY: unsure
<222> LOCATION: 1..6
<223> OTHER INFORMATION: a or c or g or t
<220> FEATURE:
<221> NAME/KEY: unsure
<222> LOCATION: 8101
<223> OTHER INFORMATION: a or c or g or t

<400> SEQUENCE: 41

```
nnnnnntgta ttttatcata ttttaaaaat caaaaaacaa aaggcagttg aggttaggca     60
tggaggttcg tgcctgtaat cccagcactt tgggaagccg aagcacgtgg atcacctgag    120
gtcaggagtt cgagaccagc ctgcccaata tggtaaaacc ctgtctctac taaaaataca    180
aaaaattagc caggcatggt ggtgggcacc tgtaatccca gctacttggg agactgaggc    240
aggagaatca cttaaacccg ggaggcgggc tgggcgcggt ggctcatgcc tgtaatccca    300
gcactttggg aggccgagac aggcggatca tgaggtcagg agatcgagat catcctggct    360
aacatggtga accccatctc tactaaaaa tacaaaaaaa attagccagg cctggtggcg    420
ggcacctgta gtcccagcta cttgggaggc tgaggcagga gaatggcgtg aacctgggag    480
```

-continued

| | |
|---|---|
| gcggcgttgc agtgagccaa gatcgcgcca ctgcactcca gcctgggcga caagagtgag | 540 |
| actccatctt aaagaaaaaa aacaaacccg ggaggcggaa attgcagtca gccgagatct | 600 |
| cgccattgca ctcaagtatg ggtgacagag caagactcca tgtcaaaaaa aaaggcagtt | 660 |
| gacaggagca aggagcctgg tgaggaagct gtggcatttg acccggctgt gttgctatgg | 720 |
| gccaggtgg tgctagtaga ggagctgagt gggaaagagc acaggggaca tgctgaaggc | 780 |
| ctgggtgtgg ggatgaggca gagattgggg gcaccttgca gggtcatagc aggtggctgt | 840 |
| ggtgagatgg aggaagacac ctggggtact gctctaggct gtcagacata cagaagctgg | 900 |
| cccagccaag cccaggggct gcaagggaca tccttttgtg tccccagtga tctgcagctc | 960 |
| tcagacaccc tcaagcacag tgcctcttgc ccagcccagc actctcagtg gggagccagg | 1020 |
| tgggagaaca ggctcggaag gggacctagg cttatgcagc gagccgggca agctggaac | 1080 |
| tggagcccag gccctggat gcccctggc ttgtggagtt ctgggatact gagggaggg | 1140 |
| gacagggcat gggagtgcgg tgctctcacc tttgacttga actcattccc caggggacag | 1200 |
| ggaggcctc ctcaggatcc acagatgccc agtctcccaa gagggcctg gtccccatgg | 1260 |
| aggaaaactc catctactcc tcctggcagg aaggtaagtt ggaggacgtg caagggcagc | 1320 |
| ctcagccccc cacacccagg gctgggtctt tttgggactg acggagctgt cctggccacc | 1380 |
| tgccacagtg ggcgagtttc ccgtggtggt gcagaggact gaggccgcca cccgctgcca | 1440 |
| gctgaagggg ccggccctgc tggtgctggg cccagacgcc atccagctga gggaggccaa | 1500 |
| ggcacccagg ccctctacag ctggccctac cacttcctgc gcaagttcgg ctccgacaag | 1560 |
| gtgaggtgca ggggtgggaa agggtgaggg gctgacagcc tggaccctcc tgctaatccc | 1620 |
| cacccgtgtg ccctgtgccc agggcgtgtt ctcctttgag gccggccgtc gctgccactc | 1680 |
| gggtgagggc ctcttcgcct tcagcacccc ctgtgcccct gacctgtgca gggctgtggc | 1740 |
| cggggccatc gccgccagcg ggagcggctg ccagagctga ccaggcccca gccctgcccc | 1800 |
| ctgccacggg ccacctctct gccctccctg gacaccccg gagagcttcg ggagatgcca | 1860 |
| ccaggacctg agccaccac gtccaggaaa atgcacctgg ccgagcccgg acccagagc | 1920 |
| ctgccgctac tgctaggccc ggagcccaac gatctggcgt ccgggctcta cgcttcagtg | 1980 |
| tgcaagcgtg ccagtgggcc cccaggcaat gagcacctct atgagaacct gtgtgtgctg | 2040 |
| gaggccagcc ccacgctgca cggtggggaa cctgagccgc acgagggccc cggcagccgc | 2100 |
| agccccacaa ccagtcccat ctaccacaac ggccaggact tgagctggcc cggcccggcc | 2160 |
| aacgacagta ccctggaggc ccagtaccgg cggctgctgg agctggatca ggtggagggc | 2220 |
| acaggccgcc ctgaccctca ggcaggtttc aaggccaagc tggtgaccct gctgagtcgt | 2280 |
| gagcggagga agggcccagc cccttgtgac cggccctgaa cgcccagcag agtggtggcc | 2340 |
| agagggagag ggtgctcccc ctgggacagg agggtgggct ggtgggcaaa cattgggccc | 2400 |
| atgcagacac acgcctgtgt ccaccctggc ctgcaggaac aaggcaggcc gcctgtggag | 2460 |
| gacctcagcc ctgccctgcc ctcctcatga atagtgtgca gactcacaga taataaagct | 2520 |
| cagagcagct cccggcaggg gcactcacgg cacacgcccc tgcccacgtt cattgcggcc | 2580 |
| aacacaagca ccctgtgccg gttccagggg cacaggtgac ctgggcctta cctgccaccc | 2640 |
| gtgggctcaa acccactgca gcagacagac gggatgaaa tcattaggac tccatgttgc | 2700 |
| tctgcacggc cgagtgacac gaagaggcag gcggagggag ctgtgaggct tacttgtcag | 2760 |
| actcaggaag gagcaacatg agggcccaac tggagacccg gaggcccgag ctggaggag | 2820 |
| gcagtggggg cggggtgcag gtggaaggga tttcagagac accctcgtcc aaaacacttg | 2880 |

-continued

```
ttccctgctg aaactccaac aatttgcaga tacttctggg aaccccaggc gtcagtctcc    2940
tcatctgtaa aggagagaga accgatgacg tatcaggcat aatccttgat gagagtttgc    3000
tgcgtgccta ctcagtgcca ggcgctgggg gacacagccg tgttcaggac agccttggtc    3060
ctgttctccg ggagccgaca ttccagggggg agagaagttt cctgaagact tccatgctgc    3120
gttccctcct ctgctcctgc tcctggcgcc atcctaggag ccagccatgc acgcaagcgt    3180
catgcctcca gggctctgac tgcccagccc ctcaccgcaa ctccacctca gctgcacaca    3240
cccttggcac atcctgaacc tcattttcat gacggacaca caattttttgc tctctcctgt    3300 ccaagcctca tcctctggcc gccacctcct tccagctcac ttcctttagt gcggccagta    3360
ccgcccctgc ctaggcatgt cgacctgcag ggaccctttt ctggctcttc gaggcctctg    3420
cccaccatcc cctctttgtt ctccatagtc ccttcccctt gttctctctc gtttcatctt    3480
actggtctgg caaagtcccc ggccttgggc gagccagacc tcctcagtgc ctgcacacag    3540
ctgcccacag ccagagaaat ccatttaagc agactgcctg catccttctt aacagtgcaa    3600
ggcaggcact ccctgccaca agagaccctg ttccctagta gggcagcttt tctcctcccc    3660
agaacctcct gtctatcccc acccaatgtc tcctcacagg catattgggg aaacaggtca    3720
ggctctccca ccgtatctgc aagtgtactg gcatccatct gtcttcttcc taccccctaca    3780 gtagaaacag tgtctgtccc cagctgtgct ctgatcccgg ctcctttcac ctcagagctt    3840
ggaaaattga gctgtcccca ctctctcctg cgcccattca tcctaccagc agcttttcca    3900
gccacacgca aacatgctct gtaatttcac attttaaacc ttcccttgac ctcacattcc    3960
tcttcggcca cctctgtttc tctgttcctc ttcacagcaa aaactgttca aaagagttgt    4020
tgattacttt catttccact ttctcacccc cattctctcc tcaattaact ctccttcatc    4080
cccatgatgc cattatgtgg ctttattag agtcaccaac cttattctcc aaaacaaaag    4140
caacaaggac tttgacttct cagcagcact cagctctggt tcttgaaaca cccccgttac    4200
ttgctattcc tcctacctca taacaatctc cttcccagcc tctactgctg ccttctctga    4260
gttcttccca gggtcctagg ctcagatgta gtgtagctca accctgctac acaaagaatc    4320
tcctgaaagc ctgtaaaaat gtccatgcat gttctgtgag tgatctacca agaaaataaa    4380 aaatttttaaa aatcaaatgc ccatgcctgg gcccacacgc aggggctctg atttcatcag    4440
tctggtaggt gggttctggg catccacgct cactggattt ccggatgatt gtagtatgca    4500
gcctaggctg ggaaccactg gcctcagcaa gccagtcatt ctccaggtgt cacagaccct    4560
ctaggtgcta atgaccccga aggtctgtct tcagtgcaca cctcccctg agctccagat    4620 ttaggaatcc cactgcacac gagacatctg gatgtggaaa agacatctcc agatcccatg    4680
ggtgaaaggg ggttggggga atggagactc gtgttcttcc aggatgtgtg tggacacaga    4740
atgcaaagcc tggagggatg ctagagccat agggaggaag atttcggctc acttattcat    4800
gcaagcactt cctgatgggt aaggtcttag agcaagctga ggccaagagg cgggcagtcg    4860
aggtgctgct gcaggcaccc ccactcccta cagtggcaag cccaagccca gcccttggca    4920
gctcaaatcc caggacacgc tgaaggtcac ccagagagtc aggggcatgg ctagaaccag    4980
aacccaggac tctggggacc cagcatggca tccttttcctt cattacaaat ctgagctgct    5040
ttgtttccta gggatttctg tgatattcca aggggactgt gggaaagaaa gtccttggaa    5100
accaccagga cgctagaggc ctggcctgga gcctcaggag tctcggccac cagagggcgc    5160
tgggtccttg tccaggtcca gttgctacgc aggggctgcc tgtgctggga ggctccccag    5220
```

-continued

```
gggacacaga ccagagcctt gcaccagccc aaggaatggg agcctggggt cctctctgct    5280
ggaggactgc caggacccc aggctgccgc ctcttccttt gctcatttgc tgtttcactt     5340
tgtcaatcct tccttctc gtgtgttcat tcacatccac tgtgtgctgg ccctggggaa    5400
atgttagata agacacatta gctgtgtgtc ttcattgtcc taacaaagaa cacaccctgg    5460
aaagagcacc gcagagagtc cccattcccc catctccctc cacacatgga atctggagat    5520
gccttttcca catccagatg tctctggtgc tgtgggattc ttaaataaac aaacatttca    5580
tacagaatgt gagatgatgg agatgctatg gggaaaagta aagcagaggg agggcctagt    5640
gtgtgatgcg ggtgaggcat ccagggattg ctgtttcagc tgtgatcagg aaaggccctg    5700
ggaggaggcc acatctgagc agagacctaa ataaagttgg aaacctgttg ctgagatatc    5760
tggagaagtg tttcaagggc cgggcaccgg gcatggtggc tcacgcctgt aatcccagca    5820
ctttgggagg ccaaggcagg tggatcgctg aggtcagga gtttgagagc agcctgacca    5880
acatggagaa accccatctc tactaaacat ataaaaatta tccgggcatg gtggttcatg    5940
cctgtagtcc cagctactcg ggaggttgag gcaggagaat cacttgaacg tgggaggcag    6000
aggttgcagc aagccgagat cacaccactg cactccagcc tggatgacag agcgagactc    6060
cgtctcaaaa aaaaaaaga aagaaaaaa gaaaaaaaa gaaaagtgtt tcaagcaggg    6120
gaactggcaa gtgagaggc cctgaggcag aaatatgctt ggcctgctgg aggaaatgtg    6180
agtgaggagg tcaggtggc tggagtggag ggagcgagtg gtaggagtca gacccagttt    6240
attcatattc tgtaggtctt aaggacttca gttttatttt gagtgcaata tgagcccact    6300
ggaatgctaa aagctgagag tgacatggtg ctgtgattct ggctttaaaa atatcacttt    6360
ggctgcttcg tgaagactct ggaagggca agggtgaaag cagggatgcc cgttaggaga    6420
ccgttacagg ggcgcaggca caaaatggca gtggctggga caatggtggc agcagcggtt    6480
agatgtgaac atgttgaagg tggaatttgc agaatctggg ggaggacaga agagaaagga    6540
taacttcatc gtttctgctg aaccagttgg ataaatgttg gtggcacttc ttgaagtgag    6600
gaaggagtta ggaaggtggg aaaggcacaa gtttgaattg ggccatgatg gtctgagata    6660
cctagtacag tggttcccca accttttggg cagaagggac cgctttcatg gaagacaatt    6720
tttccacaga ctggggtgg ggtggggatg gtttcagggt ggttcgagtg cagtacattt    6780
atcattagac tcttttttt ttttttttt tgagatagag tctcgctctg tcacccacac    6840
tggagtgcag tggagccatc ttggctcact acaacctctg ctgcccaggt tcaagtcatt    6900
ctcctgcctc agcctctcaa gtagctggga ttataggcat atgcgccacc acgcccagct    6960
aatttttgta tttttagtag agacggggtt tcaccatatt ggccaggatg gtctcgaact    7020
cctgacctca agtgatcctc ccccgcctca acctcccaaa gtgctgggt tacaggcgtg    7080 aaccactgca cccggcccat ttatcattag attctcataa ggaatgagca acctagatcc    7140
ctcgcatgca cagttcacaa tagggttcac gctcctatgg gagtctaatg ctgccgctgc    7200
actcagcttc tctggcttgc cgctgctcac cttctgctgt gcagcccagt tcctaacagg    7260
ccacaaacgg ggagttgggg acccctgatc tagtaaacat ctaggcaggg ttttggataa    7320
tggagttaga gttcctgggg agaggtcagg ctggccatga acatgggat gcctttgcat    7380 ataggtggtg ttgaaagcca caggacagta cggggtctca gggggtgagc ataaagagag    7440
gcgacatcag atggccaagg ccagaggcag aggaggatgg gaaggagggg ccagtgggc    7500 aggggggaagc tgtgaagcca gggaaaaagg gtgtttcgcg gaaaaggatc aacctggacc    7560
agtgctgccc ctaggcaggg caggatgaaa cttaaccacc acggattcca tggccccatg    7620
```

-continued

```
gcctccaggc cacaggggac cttgagaaga gagatctcag gggacgggtg cggacaagag    7680
cccgcctggc atggcttcaa gagataactg aaggaaagca agtggagacg cgataaacag    7740
acaactccct ggaggaattt tactctcgag aggagaatta aagggtagta gctggagagg    7800
gatgtggggt caagagaagg tctttaacga cgagaactct cacggcggtt tgtgcagaac    7860
agggtgggtg tgatgactgt ggatggagag ggagaactg cagcgactct gtcctaggag     7920
gaggtgatgg gccgggacca ccaagcgagt ggagggtgga cgccccttcc ctcaccccga    7980
cacccgcatg tgctcagtgt ccgtgccgcc ggccctagtg cctgggctga acgcggggcc    8040
gggactctga ggacgcctcc caggcgcgca gtccgtctgg ccaaggtgga gcgggacggc    8100
ngcttccgac ggtgcgcggg tcggctcggg gttgcaggga catccggcgt ccgctcctgc    8160
cctgttttcc tgccttcgca gagcgttgcg caactctagc tttaaacgcc cctgtccccc    8220
tcaacttgtc tcccccagcc cctctgattt acagattctg cagtcccga gggttgcgcc     8280 tacgataccg acactcgcgg cagcctgcga ggcgagtatg atcgtcccat ttttcggagt    8340
agcaaactaa ggttcagaga ctactatgtc ccaggtcggt ctggtttgaa ggtccgcttt    8400 cctctcccctc cgccagcggg cggtgcgagg gactgggcga ggcagcgctt ccctaaggag   8460
gcgacccgca gccccggccc cctcccgact ccgccccgtt gcagggcccg ggtcggcgag    8520
gcctctcagc tctaagcccg acgggacttg gtgattgggc aggacggaag agctgggtgg    8580
ggctttccac cagcggagaa agtctagtgg gcgtggtcgc gacgagggcg tggcctggtg    8640
ccccgccccc gtccgcgcgc tcaaagtgga gggtggctgt ggggcgggg tcagaacact     8700 ggcggccgat cccaacgagg ctccctggag cccgacgcag agcagcgccc tggccgggcc    8760
aagcaggtat cgacgaccgc gcgggcgtc ttgggctgga ccaggcgggc gcccggggcc     8820
tgctgaggac cacaaagggc actggggtc gtggtccagg ctgtgcttcc tccgctggc      8880 cctgcccct gcctccgccc ccgccccgc cttcctgccg ctaagccggc tgcggcgggg      8940
ccgattggcg cctgccggct tcctgcgccg gggccagtct aatgcatggg gcccgggcgg    9000
gggactaagg ggaaactgag tcacgtcggt gtgggagcag ttctgtgtgg gaggcaccac    9060
cccccactgg gctcggggaa ggatcccccct ccaagctatg cttgagggtc ccagcccca    9120 tctgtctcca caggggccgc accccactcc cgccttcccc ttcttcagca cccaggggtc    9180
ccgccctggc tcccagcagc ctcgactggt cccggaatgg ctaggaggat ccgctgcagc    9240
cgcctccctc cctcccctc cctcccctc cctcccctc cctcccctc cctcccctc         9300 cccctcgcgt cccaagcccc cgtgtgctcc ctccgctggc tctccgcaca gtgtcagctt    9360
acacgcctta tatagtccga gcaggctcca gccgcggcct gctgccggga cctggggcg     9420 ggggagagga gagccggccc ctgactcacc cggaccgccc gaggctccag gctggcttgg    9480
ggggaggccg cgccagttta gtccctcggc ccacccctgg ttgcaaagaa cctcaagcct    9540
ggattcaggc acccctcacc gttccagtcc caaggggagg ggggctgctc ctgtctttcc    9600
aaagtgaggt ccgccagcca gcagcccagg ccagcctgac aaaataccctg cctcctatgg   9660 cttgggcgtg ctcaggggct gcccgtgcct gcctggcccc tgtccaaggc tggtatcctg    9720
agctggcccg gcctgcctgc ctgcccgccc accatgctgg ccactcacct tctcttctct    9780
cctctcagga gccggcatca tggattcctt caaagtagtg ctggaggggc cagcaccttg    9840
gggcttccgg ctgcaagggg gcaaggactt caatgtgccc ctctccattt cccgggtgag    9900
cctaggtttg ggaggggggc tccccagcg gtctttcggt gcttaggtct ccagagggtg     9960
```

```
atgggggag tcctaacagg agctggtcag gggccagcag gccaggagat gtctaggtcc    10020
ggagatgtag tggtacctgc ctgccacaag gactcccaat gaggtggata ctgggaggga    10080
gcacccaggc ttctccagcc ctgcactgta cccgatgctg ttctcccaag ctcctgtggc    10140
cacctctgag ggctggaggg aggctcattg tgcaggatgg gagcctaaca tttcaggagg    10200
tatctaaact tgaggtggca atgcttggag ccaggcccca gcaggacac tgtgactata     10260 ggatttcact tcagcctcac tgccgcccag ggaatagcaa tcctcatccc gttttttccag   10320 atgagagaag aactcatgga gaggtggcgg ggctcgctca tcgagtccat ggtgaagcag    10380
ggattggaat tgaggcacag catggcgtac atttttttgtg ggtagaaggg gtctctcccc    10440
agcctatgta aggacccaca tccactgttc ccattcagga tgtggtggcc tttgaccca     10500 agcagaagtg taggacaggg ctccattcta ggggcttaac ttcagcttcc aagagcctgc    10560
cctggtgtgg gtggagctgg aggctggctc ctccctgtag caggggggatt gccttataag    10620 cccaagaatg cagccccacg ctgggatggc aacagtggc tgcggtctgc agagctgaaa     10680
agggctggcc taggcctggc ccctgaacc ccactggtgg gcctctcagc tggtcaccag     10740
gctgcagctc cagctgtatg gtccagttgt gagacacaac aaattgcctg cccagagtgg    10800
gtgaggccag cctgtcggct ggcatctctg actggcctgg gggtcaggag ggggtgggga    10860
cttcctgccc ctatatccgc ctgccccgag agacccaccc aggcgccggg tgggcaggca    10920
gctgttgtca ggaagcccaa ggcaagccca gcctggaggg gcccagaggg tcgtggcctg    10980
aggaggggct caagctggag tctgtctgta ggagctgggc gtgggggtta gggtgggcag    11040
gccagcagtg ctcttctcag gggtcctttg atggcattct cctggaacct gccccgccag    11100
cagggtagta aggcagtggt tgccctatga cacacgtccc actacatagc cctcacacag    11160
ccctgaaacc tacctgacgt cctgctccct gggaaagtgc tggcccagtg tgtctgggga    11220
gcctgaacct cagtttcttc cctgatggag atgactttca gatatggcct gttggggggca   11280 ctccgggctc cagctccctg gtcagcatcc ctggcatgtg ggcggggcca ctagctgatc    11340
ccagccctgg agttggacct gggcccacat gggtgggtga ggtgggcttt tctgagttag    11400
gccagccccc tccccctccc ctgaccccag aatggaggga ggtgggaggg caagggctg     11460 gctgtgggcc caggcctggg agatgaggta acgtctggga ctgggggggct gggctgctca    11520 ggctgactca ccccccacctc atgcagggtc cagccccctg gcttttttccc tccttggttc    11580 ctctggcctt accctgcccc tggcttgagc ccctccctgc ctctctccag ccacccgccc    11640
agcgctgtct tctgctctcc tgctgccctc cccacgctct gaacacccct catcctctgt    11700
gcttcctgcc ctcctcactc tgggaaggga agccgtcccc gccccccacc ccctctccag    11760
gagccagcta gctgcacccc aagaccccca cctcgggctc agcccacagc tcccaggagc    11820
cagccctgtg ggcagggagt ggctgggcca ggtttccctt ctactgactc accatgacct    11880
tgagtaagtc acttccccctc tggggtgtca cttccccata cacagtataa ggggttgatt    11940
tagttggatt gaactaaagg tgagggagtg gctcagggtg tctccaggtg ggctgacccc    12000
tcagttgggc cccatgctc agcagaggtg gcccacagtg gtggagcctt agggtcagag     12060
acacttcctg gctctgcctc ttactagctg ggtgacttga ggcaagttgt ttaacctctc    12120
tgtgtacatt tgcaagtgca aaatgggtaa aatcccagat tactccacaa ggttgttgga    12180
agattcagtg tcaatatgta gcatagttgg tgctcaataa actgaagcaa gtcttcttat    12240
ttagcgagtg aggaagggc cgccgagctc tcttagcctt ctgacctcct acgcaagcaa    12300
gaggtcatgt tgagcccagc tcgccttcct tttcccagtg ctgtcaagct ctgtgcctgg    12360
```

```
ctgccctgcc ctctgacatc tctctgaaac ctcttgcctc ccctctccct gcctcagctc    12420
agtctgtgca ctgacccacc tgaggagcct cctggggcca ctggcagcct ggacccccc     12480 agatccccc cacccagtga aattgtcttc cagcactgcc tcacaaaagc ctacttgatg     12540
cagtgccagg cctcttgcca gatggctggg tggtcccttta ggcttggacc cagtcaagct   12600
gccctgcctg tgttgctggg gctgggctag aggcctggaa ggggtttatc agggtcaccc    12660
tctcagggcc tgggagatac ccaatcccag acattaaaac tgccagtagc ccctctacct    12720
tcaaagccaa gtcctggtcc cttccctgg cattcaaagc catcgtaagt gaactctcac     12780
ccgctaggca gcacacgcca ttctccttta ccgaggccca ccgcttcctc aaagtcattc    12840
ctgatggtct cagctcatgc tggtggcagc catttctccc agcctactgt ctctactcat    12900
tgccacagga accagggact cccagctcaa gagcctgaag gattgggtc agggaaatt      12960 ggcagtcgag ggcttgggag tgacagccat gtatggccta cgaagtccca gctgtcaact    13020
taggtcccat tcaggcagtg ttcacaggga accgggagat aacagggcct gttcctggct    13080
ctcaaagggt cccagcagac ccctatagat ggcccccgac aggtgctggg ggtgagag      13140 gtccataaga gccccggtg gtttcgggga ggaagctgcc ccctgcatgg gccagagggc     13200
atatctggta ggtggagtgg cctgggcagg aggccagcag gagcctcaaa aggcaatggt    13260
cctcctgaaa cacttgggct ttagcctgag cgtggctgtt tgtggacatc atagcaattt    13320
ctggactgtg ggggagggtg gtggcggtga atagataagc atcgtgactg gggaagctca    13380
ggtgagcacc acctgaggga gagggtctgg cagtgaataa ataagcagtg tgactgggaa    13440
attgtgaagc tcaggtgagc gccaccacct cctgggttgc tttagtgtcc agcagctgcc    13500
tagaactatg ttgaatgaag agctctctgg gttctggaag tgggacagct ttgggtgggg    13560
cagtgttacc accgtcagcc tggcttgggt ctgcagggtc cagggcctcg gtcactttgc    13620
ttctctctcc acagctcact cctggggca aagcggcgca ggccggagtg gccgtgggtg     13680
actgggtgct gagcatcgat ggcgagaatg cgggtagcct cacacacatc gaagctcaga    13740
acaagatccg ggcctgcggg gagcgcctca gcctgggcct cagcaggtat gcgggtggac    13800
atggatgggt gcgcccgcgc tggcagtggg gatccctgcg gcccggcccg ctgtcacgct    13860
ttccttctcc tccagggccc agccggttca gagcaaaccg cagaaggtac gaggctggcc    13920
gggacatccg ggcggtgggc ggtgtgggct tggacggcca ggcctgctcg ccctcctggc    13980
acattctcgg tacccaatc cctggccggg agtggagggc agaaaccgga gctaaggcgg     14040
gtctagggcc ctggagttga ccagggct gctgcacggt cctggcacca cgcatgtccg      14100
cctgtctgtc cgcctgtctg tccgcctgct gcctcccgcc gccggcgctg cgtgctcgcc    14160
cgcactcggt cagccctcgg tcctgcgtgg actgagatcg ccactcccaa atgggcccct    14220
tgaaacctga gtcgtcctct ccccgtagcc tccaaataga gtaggggt ggggtgggg       14280 tgggggctg gagctgccgc tgtcctctgc tgcaggcgcc ccacttccac ccaggccccc     14340
accttaccct gccgcccgc cctgcccggc tgtgtctctg cccaggcctc cgccccgcc     14400 gcggaccctc cgcggtacac ctttgcaccc agcgtctccc tcaacaagac ggcccggcct    14460
ttgggcgccc ccgccgctg acagcgcccc gcagcagaat gggtacgtcg cccctgccc     14520 gccccgcccc acgccatcag gcccactgtg gccacgcc cgctgcccgc tgctgctcag     14580
tctgtgctgc gccccagccc ggcggaaccc tgcggcacgc ccctggcgg ccggggtggg    14640 gctgcaggca cagggcccct cccgaggctg tggcgccttg cagggcaccg cctggggagg    14700
```

```
ggtctctgaa tgacgccgcg cccnctgctg gcggctgggg gttgggttgt ggtgtcgggc  14760
cagctgagcc ccagacactc agtgccgcct tgtccccggc tgttctgacc cctccccgtc  14820
tttcttcctc tcctgtgtct gtcccttcgt ccctttatct gtctgtctgt cttatttcct  14880
tcacaggtgc agaccccctga caagtcagtg agccccccctc tgcctgtgcc tttcttcttc  14940
cttttggcac tctgggtggc ggccctcccc caccctggct gccctcctct ccacttcgcc  15000
ctcctgtcct ctcacctacc cgcccagcag ggctcctggc ctcacccctta cccactccct  15060
cccatcactg taacccaaac ccacatgcac caaatcctgg gaggggctgc ccccaccgcc  15120
cacccccagt gtgggttct gagccacacc ctccccacag acagccgctc cgaccgctgg  15180
tcccagatgc cagcaagcag cggctgatgg agaacacaga ggactggcgg ccgcggccgg  15240
ggacaggcca gtcgcgttcc ttccgcatcc ttgcccacct cacaggcacc gagttcagta  15300
agtgccagcc cagggcaggg ggtactttcc tcgcccccag cccaggcgtg atccctgacc  15360
ctgtgtcttt tttggtcaat gcctgcctct gctctctcag tgcaagaccc ggatgaggag  15420
cacctgaaga aatcaaggta cagggacggg caccagcccc tctcccacct cctgcctctt  15480
ccattccagc tactgccctg tgtctactcc tgaggctccc agctggggct tcaattctc  15540
ccttccttcc ttccttcctt ccttccttcc ttccttcctt ccttccttcc ttccttcctt  15600
ccttcctcc ttccttcctt ctttcatttc ttccctccct ccttccttcc ctcctccctc  15660
cctgcctccc ttccatctct ccttccttcc acttcttcct ccctctctct ctgcccctca  15720
gggaaaagta tgtcctggag ctgcagagcc cacgctacac ccgcctccgg gactggcacc  15780
accagcgctc tgcccacgtg ctcaacgtgc agtcgtagcc cggccctctc cagccggctg  15840
ccctctctgc ctcctctttt ctgttcctcc tgcccagggc accccctag tgcctccagc  15900
ttctgcctac ctcaccccc ctttcgtgcc cctggcctga gcctcctgct ggcctggccc  15960
tggccgccca cctgggttca tctgacactg ccttccctct ttgccctgtg gtactgctgt  16020
ctgccaggtc tgtgctgcct tgggcatgga ataaacattc tcagccctgc ttgctctgcc  16080
tgtcttctat ctttgtggac ctggtttgca tttggggtgt gggggtgttt cgtggttcgg  16140
actgtttggg ccctgccgtc cttgttttca gtgggagggg gtacctggca aaggggccct  16200
gccctgccat cacagatggc ttcctggcat gagggagcc ccaggagctg cctcagaagc  16260
gggagccctg cctcgtctcc cagctagaga ccgcacacca gctaactgga cattgctagg  16320
agaagctgcc cttcccatcc ctaccccagt gggacctgga atccaactcg gcagtttcca  16380
cgcccccagt catctcccgt ggggccagca ggacccaggt tgggggtgg ggccatgtca  16440
ggaagctcag ccatgcaggg ccttgaatgg cagatcttgc agccaggtgc ccaggacaga  16500
agccccagcc ccagcctcat ctacacccca ggagccctgg cctggtgaga gggagtgggc  16560
tcgggcctgg gcaagggtgg gcagcctcca ggggcatggg ggtggtgggc ttctctcagc  16620
tgcctgggc tccaccccg tcctttgggg tcctgggca cccctttaga gtcactttcc  16680
ccggcaggcc ctaccgcccc cagccctacc agccgcccgc cctgggctgt ggaccctgcg  16740
tttgccgagc gctatgcccc ggacaaaacg agcacagtgc tgacccggca cagccagccg  16800
gccacgccca cgccgctgca gagccgcacc tccattgtgc aggcagctgc cggagggggtg  16860
ccaggagggg gcagcaacaa cggcaagact cccgtgtgtc accagtgcca caaggtcatc  16920
cggtgggtgg cctgttcctg tccgaccctg gctttcccat cctgcagccc agccccacct  16980
gtctgcccac ctgtcttgcc tcagctgcga ctggggggaa taaggattca gttctcagct  17040
ggagtaggag tagggacctg ggctgggtcc tcccattctt aatcccacgc tacctacccc  17100
```

```
agcccaccca caacaactgc tagcagcatc tgccgtggcg aaatagccga agggccaacc  17160
ataggctgaa gctgcacccc tacctttgct gctctctggg caaagagggg cctgcccccct 17220 cccagcgcgt ctgcccctcc ctcctgctct ctgtctccct ctgctctcag agcatacagg  17280
cctggagcca ctccctctgt gcactgcccc gtggggccaa gcagcatcaa acaccccca   17340 gcatcagcgt gccggattct agagccttcc taattcgcag gcctggcctg ctctcatctc  17400
tgtcagctct tttttttttt tttttgaaac agagtctcac tgtgttgccc acgttggcgt  17460
gcagtggcgc gatctcggct cactgcaacc tctgcctcct gggttcaaga gattctcctg  17520
cctcagcctc ctgagtagct gggattacag gcacccgcca ccatgcctgg ctaattttgt  17580 attttttagta gagacggggt tttaccatgt tggccaggct ggtctcaaac tcctcacctc  17640
aggtgatctc aggcctgcct tggcctccca aagtgctggg actacaggtg tgagccactg  17700
tgcccagccg actctatcag ctcttgccag gtagaacagg caggccagca ggacagggca  17760
gctccagggt ttgcccaggg gcggctcagc ttttatgagg ctccagtcgt cagcccttcc  17820
tcccggggtc ctccctgctc taaagctgcc tctcctgtca ccagcagttc agtgtggcgg  17880
actggctctg taagcttcat ggctgccacg gtcacttccc aagcctgtct tctatcctat  17940
gtggaaaatg gggagaatga actgtccctc ccaaggcctc ctggtgggtg gtcagtcaac  18000
ctgaaggggg ccaagacccc cacctctctg cgtgtgctcc ctctgaccgc tctcgcctcc  18060
ctgcaggggc cgctacctgg tggcgctggg ccacgcgtac cacccggagg agtttgtgtg  18120
tagccagtgt gggaaggtcc tggaagaggg tggcttcttt gaggagaagg gcgccatctt  18180
ctgcccacca tgctatgacg tgcgctatgc acccagctgt gccaagtgca agaagaagat  18240
tacaggcgtg agtagggctg gctggcgggg aggtggtccc aagcctgtca gtgggaacga  18300
gggctgctgg gaaacccaca gtccaggtct ctccccgagt gagcctccgg gtccttacca  18360
gcgtaataaa tgggctgctg tactggcctc accctgcatt agtcaggatg ctcttaacaa  18420
atgaccatgt tcctgctcag aaaccgccca aggctgcaaa gagcaggagg accaagccag  18480
gagaagccct gggccctcct gactcccact ttgggctctc cctgccctgg tgaaatgaca  18540
gaacggccaa cttgacacgc tgaagctgct ctgtctcatg cgtcctcctc atttctggat  18600
ccagagccag ggctgccagg agtagccaga gagctctgtg tggtgatgtt catattagtg  18660
aggtttacct tgaccacgag cagtgggaaa ctcaaaataa tggtggctta tttctcatct  18720
aaaaacatcc cggggtgggt ggtctgggac tgatctggtg gacccaggct ccgccttgtt  18780
gcttgactgt tggcagcacc tgcttactta ccactcatgg tgcaagatga cacttcagcc  18840
tccgccaaaa tgctcacctt ccagccagca ggaagtcgga aggagaagaa aggggacaga  18900
gccccatggc gtccatcctt agaggatgct gccacctgaa cctctgcttt catcctgttg  18960
gtcagaaccc agtcacatga ccacacccag tggcaacgga ggctgggaaa tatagtcttt  19020
attttgggca cccatgtgtc cagcaaaact gggggttcca tcagtcggca agaacgggag  19080
agtggccgat gcagtggctg atgcttgtat cccagcactt tggaggtcg aggtgggcag   19140 atcacctgag gtcaggagtt caagaccagc ctggccaata tggtgaaacc ctgtctctac  19200
taaaaataaa aaaattagct gggtgtgctg gcgcacctgt agtcccagct acttgggagg  19260
ctgaggcagg agaatcgctt gatcttgaga ggtggaggtt gcagtgagcc aagattgtgc  19320
cactgccttc cagcctggga gacagcaaaa aaaaaaaaa aaaaaaaaa aaaaagggcc    19380 aggcacggtg gctcacacct gtaatcccag cactttggga ggccgagatg ggcggatcac  19440
```

```
gaggtcagga gattgagacc atcctggcta acacggtgaa accccatctc tactaaaaat   19500
acaaaaaaat tggccgggca tggtggagta gtcccagcta ctcggaggc tgaggcagga    19560
gaatggcgtg aacctgggag gcagagcttg cagtgagccg atcgcgcc actgcactcc     19620
agcctgggca acagagcgag actcttgtct caaaaagaaa aaagaaaga gaaatctgcc    19680
tcccagcctt gggctcctgc cctaccagcc cacaccctg gtagagcctc ctctcccacc    19740
agctcaaagc ccaagttcct tcactgtgac cttgtctgct cctctaaaac aggcaacacc   19800
agacagtgag aagagccagc cagacatggg cagaaaacct atttctgtga tctactggct   19860
gtgtgagcag gggctagttg ctctctctgg gcctcactga agagaagggt ggcactatgc   19920
tagggccggc acggttgcaa ggtagatgta agatggggta caggtgttgt ggagggcaga   19980
aatgcaccat ccgaaggcta catgtcccccc acacttatgt cttgcttggc ccacactgtt  20040
tcattttaaa atcagtagca aacaatttaa aaatcagaa gatttgcctg catgatgcag    20100
tggctcatgc ctgtaatccc agcactttgg gaggccaagg tgggaggatt gcttgagccc   20160
aggagttcaa gaccagcatg ggcaccatag caagacccct gtttctacaa aaaaaaaaa    20220
attagaaaat tagccaagtg tggtggcatg cacctgtggt cccagctact tgggaggcag   20280
agggaaagtg agatctcctg cttttttattt ctttatgtat aatgataggg tcttgctctg  20340
ttgcccaggc tggagtgcag tggcatgatc actgctcact gcagccttga tctcctgggc   20400
tcagaggatc ctcccacctc agcctcccaa atagctagga ctagaggtgc ccaccagcat   20460
gctcagcaga ttttttaaatc tttttgtaga gatgaggttt tgctatgttg cccaggctgg   20520
tctcgaactc ctggcctcga gcgatcctcc caccttggcc tcccaaagca ctgggattac   20580
agacgtgagc cactgcgccc agcagatttc tctttaacac ctagatttca gcctgagcca   20640
ggcaggcatt cctgaatgaa ccagtagtac tgctcccaga agaagaggtc ctcctccgtg   20700
tgacacagtc cccacttggc ccttgcaggg attggatctg ggatccctgg atttaaactc   20760
agggccatcc tcataacagc ctcacaaggc tgggattagc ttcccagttc acaagggaag   20820
aaaccaagac ttgagaaggt caaggtctgg ccagacccac acatcttgga ccctcatacc    20880
gcctcgaggc cccatgctgc cctctgcctg ctccagatgt gaatactgct ggccctggct    20940
ggccccggct ggccccgagg gtcctaggga tgaacagccc agcccaggga gagctcagcc    21000
ccttgtgcct ctgccccttc ccacctcctg cggaggccag tcgactcacc cacaaagggc    21060
caggcactgt ggggatagat cagctaacaa aacagttgat gcttcctgcc cttctgggcc    21120
ttacattttg gctggaagaa gaggggagag gcagactgta agcaataagc gcaataagta    21180
ggttgcctgg aagtaatgtt agatcacgtt acgaaaaaca ggaaagagca gagcgacaag   21240
tgctggggtg cgtggtgcag ggaaggcagc tggctgctgc tggtgtggtc agagtgggcc    21300
ctcatggaga agactgcatt cgagcagaaa cttgaagggg gtgaggggtg agcctagaga    21360
tatctgggc agagcagtcc aggcagaggg gacagccggt gtcaagccca ggacaggagt     21420
gtgcctggtg tgccagtttc aggcaagagg ccagtgtgca gaggcaaggt gagaacgcaa    21480
gggagagcag tggcggagac gggtgggaac gaggtcagac ctgctggcct ccagcctctg    21540
catgggcctt ggctcttgct gggagcaatg ggaagcagta cacagtttca tgcaggggga   21600
gaaggcctgt cttgggttgc aggggcacgc tgtggcagct gggatcagag agaggagctt    21660
gtaggccagt tgttatgtgg tcccacgggc cagatggcca tggcttacct cacttcaggg    21720
aggctgtgag aagcactcag aatctggatg tgccttgggg gtgggcccca ctggatttcc    21780
tggtggacct ggtgtggggt gtgagaggag ggtgtgtttg gctgcagcag acaggagaat    21840
```

```
ggagttgcca tccgcgtgat ggggatggct gtgggaggag aggtttgggg tgagggaatc   21900
aggaactgag tgctggacat ggcaagtctg aaggcgcagt ggtcgtccac tcagagacct   21960
tggagttgga gatggaggtg tgggagtcct gaacagttag atgtagtgtt taccgcgaga   22020
aggaacaggg cttgcggcca gccctcctgt gttcccgtga cccagggcag ggcaggaggg   22080
gcctgagcct gccgagtgac tgggacctcc ttccaggaga tcatgcacgc cctgaagatg   22140
acctggcacg tgcactgctt tacctgtgct gcctgcaaga cgcccatccg gaacagggcc   22200
ttctacatgg aggagggcgt gcccctattgc gagcgaggta cccactggcc agtgagggtg   22260
aggagggatg gtgcatgggg caggcatgaa tccaggtcct ctttctctct gccccccattc   22320 tcagactatg agaagatgtt tggcacgaaa tgccatggct gtgacttcaa gatcgacgct   22380
ggggaccgct tcctggaggc cctgggcttc agctggcatg acacctgctt cgtctgtgcg   22440
gtgagagccc cgcccctcga actgagcccc aagcccaccg gccctctgtt cattccccag   22500
gagatgcagg agaagttggg aagggcctc tcctgctgcc cccaacccca tgtgactggg   22560
cctttgctgt ccttagatat gtcagatcaa cctggaagga aagaccttct actccaagaa   22620
ggacaggcct ctctgcaaga gccatgcctt ctctcatgtg tgagccccct ctgcccacag   22680
ctgccgcggt ggcccctagc ctgaggggcc tggagtcgtg gccctgcatt tctgggtagg   22740
gctggcaatg gttgccttaa ccctggctcc tggcccgagc ctggggctcc ctgggccctg   22800
ccccacccac cttatcctcc cacccccactc cctccaccac cacagcacac cgatgctggc   22860
cacaccagcc cccttttcacc tccagtgcca caataaacct gtaccagct gtgtcttgtg   22920 tgcccttccc ctgtgcatcc ggaggggcag aatttgaggc acgtggcagg gtggagagta   22980
agatggtttt cttgggctgg ccatctgggt ggtcctcgtg atgcagacat ggcgggctca   23040
tggttagtgg aggaggtaca ggcgagaccc catgtgccag gcccggtgcc cacagacatg   23100
aggggagcca ctggtctggc ctggcttgga ggttagagaa gggtagttag gaagggtagt   23160
tagcatggtg gctcatgcct gtgatcccag cactttggaa ggccaaggtg ggcagatcgc   23220
ttgaggtcag gagttcgaga cctcatggcc aacacggtga acagcgtct ctagtaaaaa   23280 tacaaaaatt agccgagtgt ggtggggcat gcctgtaatc ccagccactc aggaggctga   23340
ggcgggaaaa tcacttgaac ctgggaagtg gaggttgcag tgagctgaga tcacaccact   23400
gcgcgcgagc ctgggtggca gatggcagag cgagaccctg cttcaaaaaa aaaaaaaaa   23460 aaaaaaaaaa gaagggtagt tgtagttggg ggtggatctg cagagatatg gtgtggaaaa   23520
cagcaatggc cacagcaaag tcctggaggg gccagctgcc gtccaaacag aagaaggcag   23580
ggctggagag ggtagccctt aggtcctggg aagccacgag tgccaggcag tagagctggg   23640
gctgtctctt gaggttaggg cagggcaagg cacagcagag tttgaaatag gtttgtgttg   23700
tattgcagaa aagaggcccc agaacactga gggagtgcag gagggaggct gggaggagga   23760
gttgcagcag ggcctagggg cgggggccag gcaagggagg ggcagagagt aatatggcag   23820
agatgggacc cagtggcagg tccgggggat gagggatgga gagaaggaca ggagcgttgc   23880
caggcatctg gcctatacca gacatgctca cgctgtctcc cgcgaacctc ctagcaacct   23940
tgcgccgttg tctgcaatca cttatttcat tttttctttt ttaactttaa ttttttttgt   24000
ttttaagaga caggatctcc ctaggttgcc cgggctggtt tcaaactcct gggctcaagc   24060
aattcttcct ccctagcccc aaagtgctgg cattacaggt gtgagccacc atgcctggcc   24120
cacttatttt ctagatgagg cacagaaaga ttgggagact tgaccaaggt cacgctgtca   24180
```

```
ttgagccatg agccagacta gaatccaggc ctgaagctgg gtgcgctgtc ccaggactgg    24240
ctggcactga gtaccatttg ccagcgagca tctctctggg aagctgactt ctgcccggta    24300
cctggaggac tgtagacctt ggtggtggcg ccgtcactct ggggcttcct gcctcccact    24360
gatgcccgca ccaccctaga gggactgtca tctctcctgt cccaagcctg gactggaaag    24420
actgaagaga agccttaagt aggccaggac agctcagtgt gccatggctg cccgtccttc    24480
agtggtccct ggcatgagga cctgcaacac atctgttagt cttctcaaca ggcccttggc    24540
ccggtcccct ttaagagacg agaagggctg ggcacggtga ctcacacctc taatcccagc    24600
actttggaag gctgaggctg gagaagggct ccagcttagg agttcaggac cagcctgggc    24660
aacatggtga gaccctgttt tgttttgttt tttgttttt tgagatggag tcttgctctg    24720
tcgcccaggc tggagtgcag                                                24740
```

<210> SEQ ID NO 42
<211> LENGTH: 25
<212> TYPE: DNA
<213> ORGANISM: Rattus norvegicus

<400> SEQUENCE: 42

```
gcactacctt gaaggaatcc atggt                                             25
```